United States Patent
Kim et al.

(10) Patent No.: US 11,013,836 B2
(45) Date of Patent: May 25, 2021

(54) INORGANIC BIODEGRADABLE SUBSTRATES FOR DEVICES AND SYSTEMS

(71) Applicant: THE CURATORS OF THE UNIVERSITY OF MISSOURI, Columbia, MO (US)

(72) Inventors: Chang-Soo Kim, Rolla, MO (US); Richard K. Brow, Rolla, MO (US); Delbert E. Day, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 388 days.

(21) Appl. No.: 15/625,534

(22) Filed: Jun. 16, 2017

(65) Prior Publication Data

US 2017/0360997 A1    Dec. 21, 2017

Related U.S. Application Data

(60) Provisional application No. 62/351,088, filed on Jun. 16, 2016.

(51) Int. Cl.

| | |
|---|---|
| *B32B 15/04* | (2006.01) |
| *B32B 17/06* | (2006.01) |
| *A61L 31/14* | (2006.01) |
| *A61L 31/02* | (2006.01) |
| *A61K 41/00* | (2020.01) |
| *C03C 3/14* | (2006.01) |
| *C03C 13/04* | (2006.01) |
| *C03C 3/16* | (2006.01) |

(Continued)

(52) U.S. Cl.
CPC .......... *A61L 31/148* (2013.01); *A61B 5/4566* (2013.01); *A61K 41/0057* (2013.01); *A61L 31/026* (2013.01); *A61N 5/062* (2013.01); *A61N 5/0603* (2013.01); *C03C 3/14* (2013.01); *C03C 3/16* (2013.01); *C03C 4/0014* (2013.01); *C03C 13/048* (2013.01); *A61B 2562/0247* (2013.01); *A61N 2005/063* (2013.01)

(58) Field of Classification Search
CPC . C03C 4/0014; C03C 2213/02; A61L 31/148; A61N 2005/063
USPC .......................... 428/426, 427, 428, 432, 688
See application file for complete search history.

(56) References Cited

U.S. PATENT DOCUMENTS

| | | | | |
|---|---|---|---|---|
| 4,604,097 A | * | 8/1986 | Graves, Jr. ........... | A61C 8/0012 106/35 |
| 4,664,473 A | * | 5/1987 | Gannon ................ | C03C 13/046 385/126 |

(Continued)

FOREIGN PATENT DOCUMENTS

| | | | |
|---|---|---|---|
| CN | 103964696 | * | 8/2014 |
| GB | 2461743 | * | 1/2010 |
| WO | WO2008035088 | * | 3/2008 |

OTHER PUBLICATIONS

CN 103964696 Machine translation.*

*Primary Examiner* — Lauren R Colgan
(74) *Attorney, Agent, or Firm* — Stinson LLP

(57) ABSTRACT

Disclosed are biodegradable glass substrates that are useful as functional elements of solid-state devices. In particular, biodegradable glass substrates having a rapidly degradable glass and a slowly degradable glass provide a structural platform that completely dissolves following a desired operational lifetime of devices such as implanted electronic devices, implanted sensor devices, and optical fibers.

5 Claims, 25 Drawing Sheets

(51) Int. Cl.
*C03C 4/00* (2006.01)
*A61N 5/06* (2006.01)
*A61B 5/00* (2006.01)

(56) References Cited

U.S. PATENT DOCUMENTS

| | | | | |
|---|---|---|---|---|
| 5,250,488 | A * | 10/1993 | Thelohan | C03C 3/089 501/36 |
| 6,374,641 | B1 * | 4/2002 | Chu | C03B 37/01205 65/385 |
| 6,379,648 | B1 * | 4/2002 | Day | C03C 3/15 424/1.29 |
| 6,517,857 | B2 * | 2/2003 | Ylanen | A61L 27/54 424/422 |
| 10,507,263 | B2 * | 12/2019 | Nazhat | A61L 27/52 |
| 10,676,713 | B2 * | 6/2020 | Deng | C03C 3/16 |
| 2001/0041325 | A1 * | 11/2001 | Ylanen | A61L 27/50 433/201.1 |
| 2002/0139147 | A1 * | 10/2002 | Janas | C03C 4/0007 65/376 |
| 2003/0153972 | A1 * | 8/2003 | Helmus | A61L 31/10 623/1.15 |
| 2003/0198660 | A1 * | 10/2003 | Janas | A61L 27/427 424/423 |
| 2004/0258732 | A1 * | 12/2004 | Shikinami | A61L 27/446 424/426 |
| 2005/0079226 | A1 * | 4/2005 | Gonda | C03C 3/112 424/602 |
| 2005/0118236 | A1 * | 6/2005 | Qiu | A61L 27/34 424/443 |
| 2010/0111487 | A1 * | 5/2010 | Aitken | C03C 3/17 385/141 |
| 2010/0249912 | A1 * | 9/2010 | Gibbons, Jr. | A61F 2/82 623/1.38 |
| 2011/0014262 | A1 * | 1/2011 | Jung | C03C 4/0035 424/423 |
| 2011/0106255 | A1 * | 5/2011 | Liu | A61F 2/3094 623/16.11 |
| 2011/0172519 | A1 * | 7/2011 | Cao | A61B 5/06 600/424 |
| 2013/0090521 | A1 * | 4/2013 | Lau | A61L 31/145 600/30 |
| 2014/0271779 | A1 * | 9/2014 | Bagga | A61L 27/46 424/426 |
| 2014/0272418 | A1 * | 9/2014 | Jung | A61L 27/54 428/410 |
| 2014/0277578 | A1 * | 9/2014 | Day | A61L 27/34 623/23.72 |
| 2015/0105748 | A1 * | 4/2015 | McBride | A61L 27/24 604/500 |
| 2015/0155678 | A1 * | 6/2015 | Jiang | G02B 6/02395 385/126 |
| 2015/0328364 | A1 * | 11/2015 | Hill | A61L 27/54 424/489 |
| 2016/0245990 | A1 * | 8/2016 | Boyden | A61N 5/0601 |
| 2017/0274118 | A1 * | 9/2017 | Nazhat | A61L 27/446 |
| 2017/0360997 | A1 * | 12/2017 | Kim | A61L 31/148 |
| 2018/0265683 | A1 * | 9/2018 | Shimizu | C08K 5/34922 |
| 2019/0099522 | A1 * | 4/2019 | Preiss-Bloom | A61L 27/50 |
| 2019/0161392 | A1 * | 5/2019 | Deng | A61Q 11/00 |

\* cited by examiner

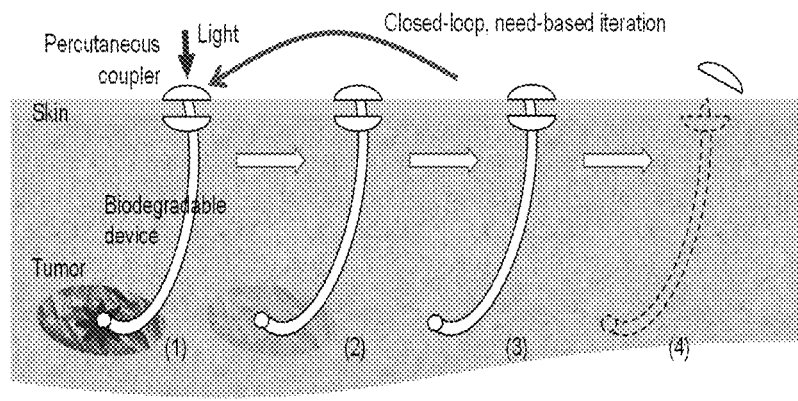
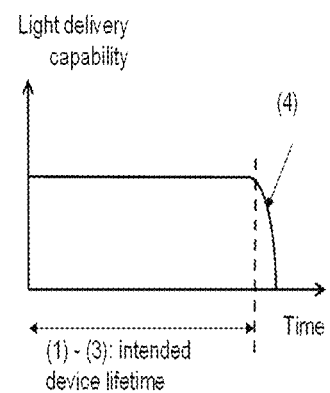
FIG. 5A  FIG. 5B
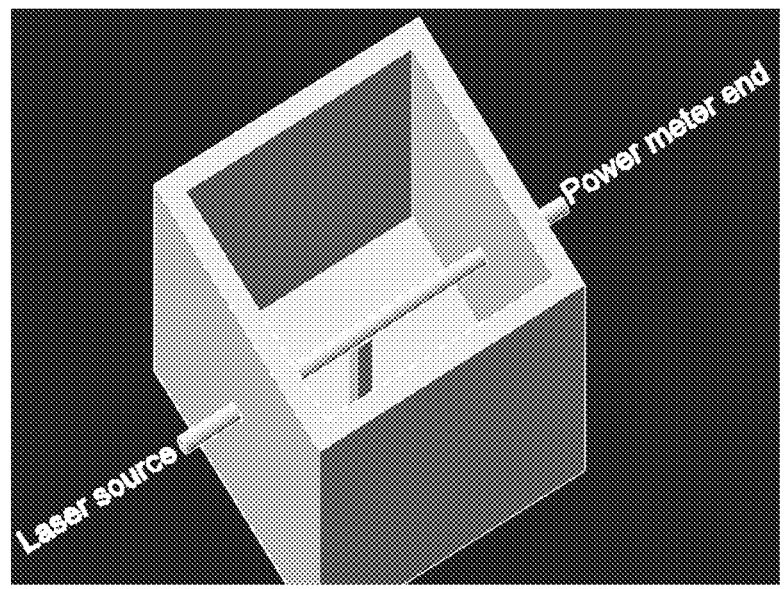
FIG. 6

INORGANIC BIODEGRADABLE SUBSTRATES FOR DEVICES AND SYSTEMS

CROSS REFERENCE TO RELATED APPLICATIONS

This application claims priority to U.S. Provisional Application No. 62/351,088 filed on Jun. 16, 2016, which is hereby incorporated by reference in its entirety.

BACKGROUND OF THE DISCLOSURE

The present disclosure relates generally to biodegradable devices. More particularly, the present disclosure relates to biodegradable glass components for use in biodegradable devices with controllable structural degradation. The present disclosure also relates to biodegradable optical fibers with controllable structural degradation. The present disclosure also relates to biodegradable devices for monitoring intervertebral pressure.

Implantable medical devices are placed inside or on the surface of the body to replace missing body parts, deliver medications, monitor body functions and provide support to organs and tissues. Implants can be permanently or temporarily placed in the body. After their intended operational lifetime, temporary devices either lose their functionality or become unnecessary. These devices are left inside the body unless removed by an additional surgical operation. This may cause significant electromagnetic and/or biomechanical safety concerns, latent complications at the implanted sites, and possible ethical issues.

Photodynamic therapy (PDT) is an emerging therapeutic modality for cancers and infectious diseases based on the light-induced cell death. However, PDT applications are mainly limited to surface treatments, application of the highest possible dose of light in a single dose (as opposed to lower doses administered over the course of multiple treatments) and low efficiency for large solid tumors.

Biodegradable devices involve implanted devices with limited lifetime that lose functionality and degrade/resorb at the end of their intended operational lifetime. Biodegradable devices are typically composed of biodegradable organic materials and biodegradable metals/semiconductors. The main advantage of using such devices is that it does not need to be removed from the body by additional surgery. The operational lifetime of these biodegradable implants can be modified by altering the chemical composition of the constituent materials from which the devices are made. Hence biodegradable implant is an advanced option for temporary medical intervention and monitoring.

Glass is an excellent material for the dielectric packaging layers. It has a low temperature coefficient and hysteresis, little dielectric aging, zero piezoelectric noise and low dielectric loss (i.e. dissipation factor). Fusion bonding of conventional glass wafers (e.g. silicate-based PYREX glass) is a common method for packaging electronic and MEMS devices. Biodegradable glasses are a class of materials that react in vivo and change their chemical composition when in contact with living tissue, allowing ingrowth of cells to become a part of the tissue itself and eventually resorbed.

Short-term biodegradable devices can be beneficial to a wide range of biomedical applications. Accordingly, there exists a need for additional biodegradable devices, materials for use in biodegradable devices, and methods for preparing biodegradable devices.

BRIEF DESCRIPTION OF THE DISCLOSURE

In one aspect, the present disclosure is directed to an inorganic biodegradable substrate. The inorganic biodegradable substrate includes a rapidly degradable glass and a slowly degradable glass.

In another aspect, the present disclosure is directed to a biodegradable device comprising an inorganic biodegradable substrate, the inorganic biodegradable substrate comprising a rapidly degradable glass and a slowly degradable glass.

In another aspect, the present disclosure is directed to a biodegradable optical fiber. The optical fiber includes a rapidly degradable glass core and a cladding. The cladding comprises a slowly degradable glass.

In another aspect, the present disclosure is directed to a biodegradable implantable intervertebral pressure sensor. The implantable intervertebral pressure sensor comprises a glass substrate comprising a rapidly degradable glass and a slowly degradable glass.

In another aspect, the present disclosure is directed to a biodegradable packaging assembly comprising a plurality of glass substrates, wherein at least one of the plurality of glass substrates comprises a rapidly degradable glass and a slowly degradable glass.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 4A depicts the scattering parameter. FIG. 4B depicts the resonant frequency. FIG. 4C depicts the peak magnitude.

FIGS. 5A and 5B illustrate the biodegradable optical fiber operation implanted for photodynamic therapy for cancer. FIG. 5A depicts four stages of the biodegradable optical fiber during tumor treatment to degradation of the biodegradable optical fiber. FIG. 5B depicts the "sudden failure" of the biodegradable optical fiber after the designed device lifetime (i.e., intended therapeutic period).

FIG. 6 depicts a conceptual diagram of transmission through a fiber during dissolution.

(FIG. 23A) Device 1, (FIG. 23B) Device 2, (FIG. 23C) Device 3.

DETAILED DESCRIPTION

Figure 1:
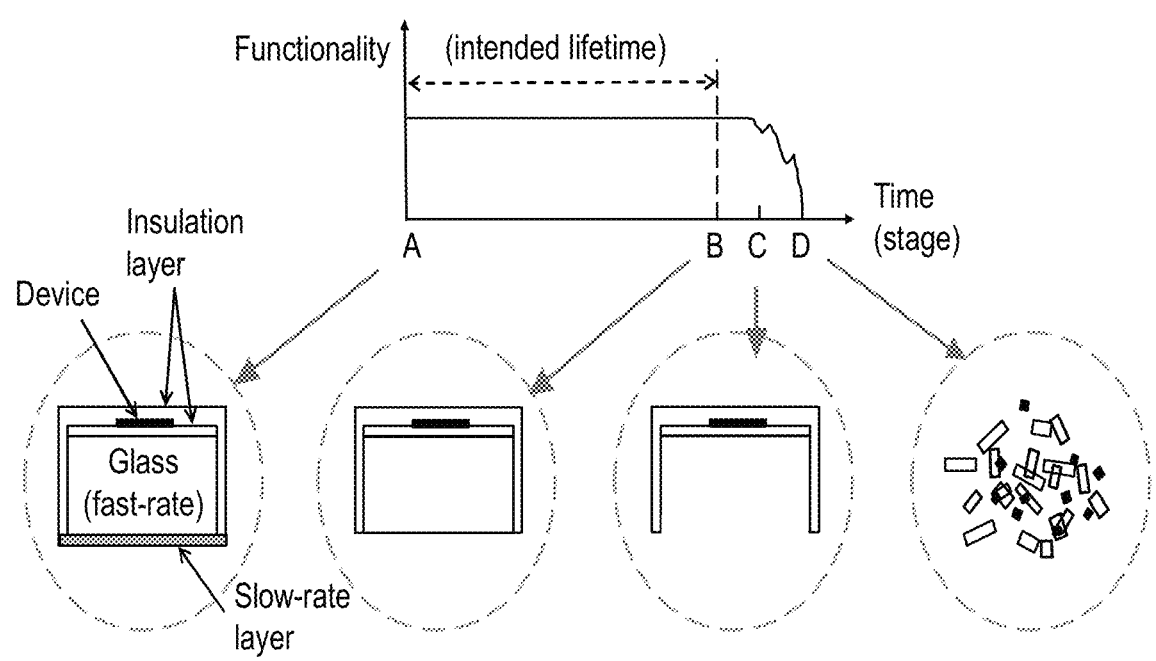
FIG. 1 depicts the conceptual device functionality versus time. Rapid failure after the intended operational lifetime: initial structure (stage A), dissolution of slow-rate glass film (e.g. several months) (stage B), dissolution of fast-rate glass substrate (e.g. 1-2 days) (stage C) and physical disintegration of crust insulation and device layers (stage D).

Unless defined otherwise, all technical and scientific terms used herein have the same meaning as commonly understood by one of ordinary skill in the art to which the disclosure belongs.

In one aspect, the present disclosure is directed to an inorganic biodegradable substrate. The inorganic biodegradable substrate includes a rapidly degradable glass and a slowly degradable glass.

In some embodiments, the slowly degradable glass substantially surrounds the rapidly degradable glass. As used herein, "surrounds" refers to enclosing on all surfaces. Thus, in embodiments wherein the slowly degradable glass substantially surrounds the rapidly degradable glass, the slowly degradable glass encloses the rapidly degradable glass on all surfaces (i.e., top surface, bottom surface, and side surfaces). In other embodiments, the slowly degradable glass contacts a portion of the rapidly degradable glass. Thus, in embodiments wherein the slowly degradable glass contacts a portion of the rapidly degradable glass, the slowly degradable glass can contact a top surface, a bottom surface, a side surface and combinations thereof, but at least a portion of a surface of the rapidly degradable glass is not in contact with a slowly degradable glass.

Glasses are compound materials composed of many glass-forming oxides including $SiO_2$, $B_2O_3$, $P_2O_5$, $Na_2O$, $K_2O$, and $CaO$, etc.

Particularly suitable rapidly degradable glasses include borate-based glasses and phosphate-based glasses. As known to those skilled in the art, "borate-based glasses" include glass materials of generally include higher concentrations of $B_2O_3$ and $Na_2O$ than other ingredients, (e.g., $B_2O_3$:$Na_2O$:all others=69:31:0 wt %). As known to those skilled in the art, "phosphate-based glasses" generally include higher concentrations of $P_2O_5$ and $Na_2O$ than other ingredients (e.g., $P_2O_5$:$Na_2O$:all others=50:20:30 wt %). As used herein, "rapidly degradable glass material" refers to glasses having reaction rates of about millimeters per day.

Particularly suitable slowly degradable glasses include silicate-based glasses. As known to those skilled in the art, "silicate-based glasses" generally include higher concentrations of $SiO_2$ than other ingredients (e.g., $SiO_2$:all others=53:47 wt %). As used herein, "slowly degradable glass" refers to reaction rates of about nanometers per day.

The degradation rate of the inorganic biodegradable substrate can be controlled. The degradation rate can be controlled by adjusting the composition of the rapidly degradable glass, the composition of the slowly degradable glass, and combinations thereof. The degradation rate can also be controlled by adjusting the thickness of the slowly degradable glass. Degradation can be determined by the time duration for dissolution in a solution such as saline and simulated body fluid, for example.

The biodegradable glass can be fabricated in three-dimensional scaffolds.

In some embodiments, the inorganic biodegradable substrate further includes a chemical modification. A particularly suitable chemical modification is silanization.

In one aspect, the present disclosure is directed to a biodegradable device comprising an inorganic biodegradable substrate. The inorganic degradable substrate includes a rapidly degradable glass and a slowly degradable glass.

The slowly degradable glass can be applied to at least one surface of the rapidly degradable glass. In another embodiment, the slowly degradable glass can be applied to the entire surface of the rapidly degradable glass.

Other device components can be built or attached directly on at least one surface of the rapidly degradable glass. Device components can be protected by applying an insulating layer, for example. Suitable insulating layers can include silicon-based films such as, for example, $SiO_2$ and $Si_3N_4$. Upon degradation of the entire inorganic biodegradable substrate, the components of the device can structurally disintegrate because of the lack of mechanical support. Suitable device components can be silicon-based biodegradable electronics, biodegradable films (e.g., silver, magnesium, etc.) and combinations thereof.

The inorganic biodegradable substrate as described herein provides a structural platform on which thin film devices can be built. Structural degradation of the inorganic biodegradable substrate having a rapidly degradable glass and a slowly degradable glass results in intentional failure of the device.

In some embodiments, the inorganic biodegradable substrate of the biodegradable device further includes a chemical modification. A particularly suitable chemical modification is silanization.

In another aspect, the present disclosure is directed to a biodegradable optical fiber. The optical fiber includes a biodegradable glass core and a biodegradable glass cladding.

Suitable biodegradable glasses for preparing the biodegradable glass core include rapidly degradable glasses with high refractive indices. Suitable biodegradable glasses for preparing the biodegradable glass core include, for example, phosphate-based glasses, borate-based glasses, and combinations thereof. Suitable biodegradable glasses with requisite high refractive index, fast dissolution rate and biocompatibility for preparing the biodegradable glass core include, for example, those having a higher concentration of heavier oxides such as SrO and $K_2O$ to increase the refractive index. In addition, the relative concentrations of glass-forming oxides such as $SiO_2$, $B_2O_3$, $P_2O_5$, and combinations thereof, which generally decrease refractive indices, can be reduced. An example is a phosphate-based glass material with a high concentration of SrO (e.g., $P_2O_5$:SrO:all others=50:15:35 wt %). At the same time, these compositional variations are also intended to impart a faster dissolution rate for the core glass than the cladding.

As used herein, "cladding" refers to a layer of glass material of lower refractive index and slower dissolution rate in contact with a core material of higher refractive index and faster dissolution rate. Suitable glasses for cladding include lower concentration of heavier oxides than that of core and higher concentrations of glass-forming oxides than that of core. An example is a phosphate glass material without SrO (e.g., $P_2O_5$:SrO:all others=50:0:50 wt %). At the same time, these compositional variations are also intended to impart a slower dissolution rate for the cladding glass than the core. The operational lifetime of an optical fiber can be controlled by varying the thickness of the cladding, by varying the composition of the cladding layer, and combinations thereof. Suitable biodegradable glasses for preparing the biodegradable glass cladding include slowly degradable glasses with low refractive indices.

The biodegradable optical fiber can further include a coating. The coating can be applied to the cladding to provide strength, absorb shock and provide protection. Suitable coating materials are biodegradable materials such as biodegradable plastics.

The biodegradable optical fiber can be of any desired diameter. Suitable fiber diameter can range from about 5 µm to about 250 µm.

The biodegradable optical fiber can be of any desired length.

In some embodiments, the biodegradable optical fiber further includes a chemical modification. A particularly suitable chemical modification is silanization.

The degradation rate of the biodegradable optical fiber can be controlled. The degradation rate can be controlled by adjusting the composition of the glass. The degradation rate can also be controlled by adjusting the diameter of the glass. Degradation of the biodegradable optical fiber can be determined by submerging a fiber in a solution such as phosphate buffered saline and measuring the diameter of the optical fiber over time.

The optical transmission property of the optical fiber can be controlled by varying the properties the biodegradable glass core (diameter, refractive index, etc.), by varying the difference of refractive indices at the interface of the biodegradable glass core and the biodegradable glass cladding, and combinations thereof. The biodegradable glass cladding with a lower refractive index and slow reaction rate is first exposed to surrounding body tissue or tissue fluid. The optical fiber is fully functional until the biodegradable glass cladding is dissolved by the tissue or fluid.

The biodegradable optical fiber can be coupled with an optical coupler such that a light source can be connected to deliver light as needed from outside a subject's body. Other devices known to those skilled in the art can be coupled to the biodegradable optical fiber.

Performance of the biodegradable optical fiber of the present disclosure demonstrates viability for delivering the light for a certain operational lifetime before structural disintegration of the optical fiber occurs. Potential applications for the biodegradable optical fiber include photodynamic therapy (PDT) for deep-seated inoperable tumors and infected tissues without additional surgical procedures for removing the optical fiber. Biodegradable light-guiding devices (e.g. optical fibers) can deliver localized optimal dose of light to deep locations (~several inches). Although interstitial illumination with laparoscopes is conducted as an intraoperative adjuvant treatment, it is mostly limited to single therapy that requires repeated surgeries if the cancer recurs. In contrast to interstitial illumination, implantable biodegradable optical fibers with percutaneous couplers can serve long time monitoring and perform necessary therapeutic procedures with appropriate structure during the intended lifetime. The biodegradable fibers do not have any concern for surgical operation for removal. In addition to this, biodegradable hollow fiber can be formed to deliver photosensitizer and oxygen while acting as light guiding device.

In another aspect, the present disclosure is directed to a biodegradable implantable intervertebral pressure sensor. The implantable intervertebral pressure sensor comprises a inorganic biodegradable substrate including a rapidly degradable glass and a slowly degradable glass.

Suitable rapidly degradable glasses are described herein.

Suitable slowly degradable glasses are described herein.

As disclosed herein, in some embodiments, the slowly degradable glass can substantially surround the rapidly degradable glass. As also disclosed herein, in other embodiments, the slowly degradable glass can contact a portion of the rapidly degradable glass.

In some embodiments, the inorganic biodegradable substrate further includes a chemical modification. A particularly suitable chemical modification is silanization.

In another aspect, the present disclosure is directed to a biodegradable packaging assembly for implanted electronic devices. The biodegradable packaging assembly includes a plurality of inorganic biodegradable substrates, wherein at least one inorganic biodegradable substrate includes a rapidly degradable glass and a slowly degradable glass.

Suitable rapidly degradable glasses are described herein.

Suitable slowly degradable glasses are described herein.

As disclosed herein, in some embodiments, the slowly degradable glass can substantially surround the rapidly degradable glass. As also disclosed herein, in other embodiments, the slowly degradable glass can contact a portion of the rapidly degradable glass.

The biodegradable packaging assembly can include two, three, four, or more inorganic biodegradable substrates as desired during routine design choice. The glass substrate can include a fast-rate glass (rapidly degradable), a slow-rate glass (slowly degradable), and combinations thereof. Other suitable combinations of inorganic biodegradable substrates can include substrates of fast-rate glass without a slow-rate glass, and slow-rate glass without fast-rate glass. Electronic chips or thin film devices can be positioned on one glass substrate. Bioinert spacers can be positioned on the glass substrate to surround the chips or device as well as maintain separation between each glass substrate. The second (third, fourth, etc.) glass substrate is positioned on top of the spacer and device. Optionally, the glass substrates can be bonded with the spacer and/or device.

One inorganic biodegradable substrate can serve as mechanical carrier element, while a second glass substrate can serve as capping element. A spacer can be used to maintain space between each inorganic biodegradable substrate. A spacer can also be used to form a cavity to locate the device between inorganic biodegradable substrate. Suitable spacer material includes bioinert polymers, such as polydimethyl siloxane (PDMS). This spacer with a small volume, typically with a thickness about one millimeter and a diameter less than one centimeter, remains after all other elements are biodegraded. It does not cause any biohazard issue due to its bioinertness. The biodegradable packaging assembly can intentionally degraded after a designed operational lifetime.

EXAMPLES

Example 1

In this Example, a glass substrate device using a glass substrate having a rapidly degradable (fast reacting) glass and a slowly degradable (slow reacting) glass were analyzed to determine functionality over time when exposed to body fluids.

FIG. 1 illustrates the expected behavior of a glass substrate device exposed to body fluids. The major portion of the substrate is made of a fast reacting glass material. The bottom layer is a slowly reacting glass film. It is consumed during a presumed lifetime (i.e., A to B stage) with the active device being fully functional due to its top insulation layer. The lifetime of the device can be manipulated by adjusting the compositions and thickness of the bottom slowly reacting glass layer. The dissolution of the entire glass substrate occurs rapidly once exposed to solution, leaving only a top layer. This crust layer is expected to structurally disintegrate without mechanical support. To prevent or reduce false results and safety concerns caused by continued use, a short duration of failure (i.e., B to D stage) was designed.

The glass substrates were manually prepared. Borate glass was prepared by melting sodium tetraborate (12305, anhydrous 99.5%, Alfa Aesar) in a platinum crucible at 1,000° C. for 30 minutes. The melt was poured into a stainless steel cylindrical mold and annealed at 450° C. for 30 minutes to form a glass rod (14 mm diameter, 30 mm). Sliced circular substrates were mounted on aluminum holders and ground using silicon carbide foils (180 to 1200 grit sizes, Struers) followed by polishing with a diamond media (DP spray P, Struers). The final surface roughness was approximately 0.25 μm measured by atomic force microscopy (Nanoscope Ma, Digital Instrument).

Figure 2A:
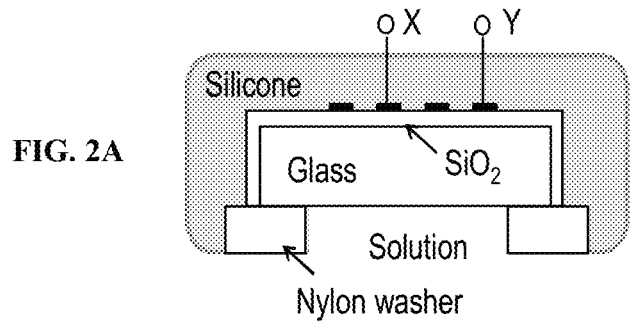
FIG. 2A depicts a cross sectional view of an exemplary spiral thin film device after encapsulation to demonstrate stages B to D in FIG. 1.

A prototype device illustrated in FIG. 2A was prepared without the slow rate layer to demonstrate the B to D stages in FIG. 1. The top and side surfaces of the glass substrates were coated with a silicon dioxide ($SiO_2$) blanket insulation layer (1 μm thick) by sputtering (Discover 18, Denton Vacuum). A spiral coil device (2.4 mm diameter, 0.2 mm line width, 0.15 mm line spacing) was fabricated with a gold layer (120 nm thick) deposited by sputtering (Bio-Rad E5400 flash coater) and patterned using a stainless steel shadow mask (4 mil thick). An SMA RF connector (0731000115, Molex) was connected to the device with silver paste (Z04969, SPI). The entire SMA connector was encapsulated in silicone (3140, Corning). A nylon washer (11 mm inner diameter, 0.5 mm thick) was glued at the bottom surface with silicone to ensure a fixed exposed area.

All dissolution tests were conducted in a simulated body fluid (SBF) solution (pH 7.4). The device was submerged in a 1 L solution placed in an incubator (Heratherm, Thermo Scientific) at 37° C. and tested for dissolution behavior. For monitoring the change in DC and AC impedance levels during dissolution, the device was connected to an electrochemical potentiostat (Femtostat, Gamry). The scattering parameter (S11) was monitored in an RF frequency range with a vector network analyzer (VNA) (E8753, Agilent). A 12-inch 50 ohm cable was connected to extend the connectivity up to the VNA. Since the VNA was calibrated only at the port while the device was present after the cable, the 1-port 3-term error model was used to obtain the actual response of the device.

Figure 2B:
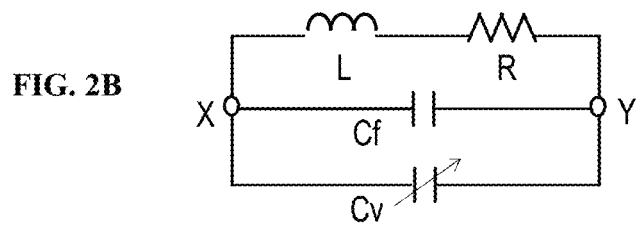
FIG. 2B depicts a simplified model of the device (L: inductance of spiral film, R: series resistance along spiral film, $C_F$: fixed capacitance through $SiO_2$ and silicone; $C_V$: variable capacitance through glass and solution).

Microwave studio (Computer Simulation Technology) was used to simulate the resonance behavior of the RLC model shown in FIG. 2B. Inductance L was calculated by a data fitted monomial expression, whereas series resistance R was measured with a multi-meter. Complex dielectric constants of the glass and solution were calculated from S11 parameter using waveguide method with the same VNA. Dielectric properties of $SiO_2$ and silicone were taken from literature. Utilizing these values, two parasitic capacitive elements, $C_F$ and $C_V$, were calculated. The calculated resonance frequency was 2.1 GHz similar to the range of other biodegradable resonance devices.

Figure 2C:
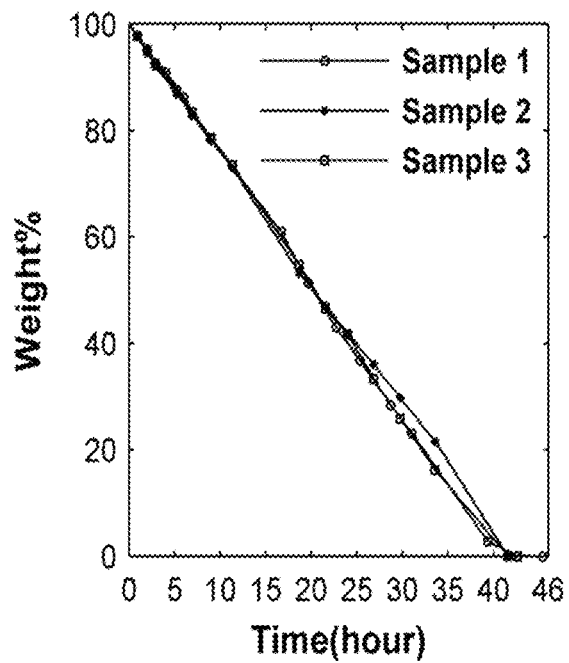
FIG. 2C depicts the dissolution behavior of bare glass substrates (2.7 mm thick, 14 mm diameter, no coating/encapsulation) in a simulated body fluid (SBF) solution (pH 7.4 at 37° C.).

FIG. 2C shows the rapid weight loss during the course of dissolution of bare glass substrates without any coated layer. The linear loss rate was approximately 5.5 mg/hour with an initial surface area of 4.35 $cm^2$. This rate was moderately higher than those of the borate glasses containing silicates. FIG. 2C represents the rapid failure after a presumed lifetime (i.e., t=0 hour being the onset of stage B in FIG. 1.) since the bare substrates had no protective slow-rate layer. Although each substrate prepared manually was used as a single "dice" at this phase, it is readily within the skill of one skilled in the art to mass-produce large diameter "wafers". Therefore, the biodegradable glass substrate provides an excellent candidate that maintains the structural integrity to support the devices during use followed by a rapid disintegration.

Figure 3A:
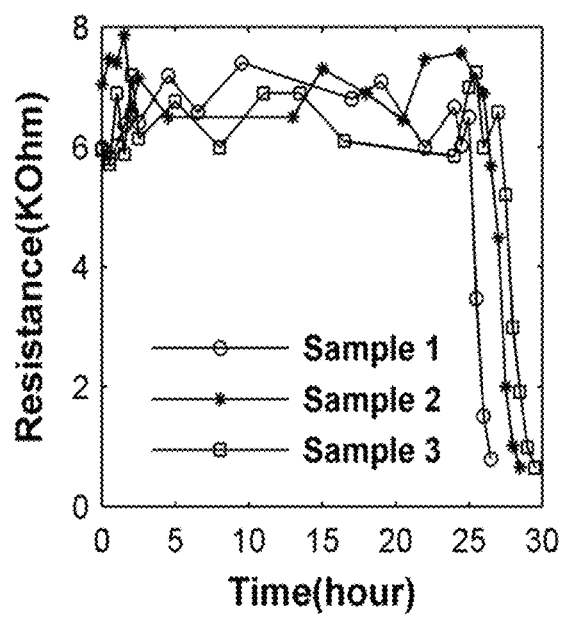
FIGS. 3A and 3B depict DC resistance (FIG. 3A) and AC impedance (FIG. 3B) behavior over time.
Figure 3B:
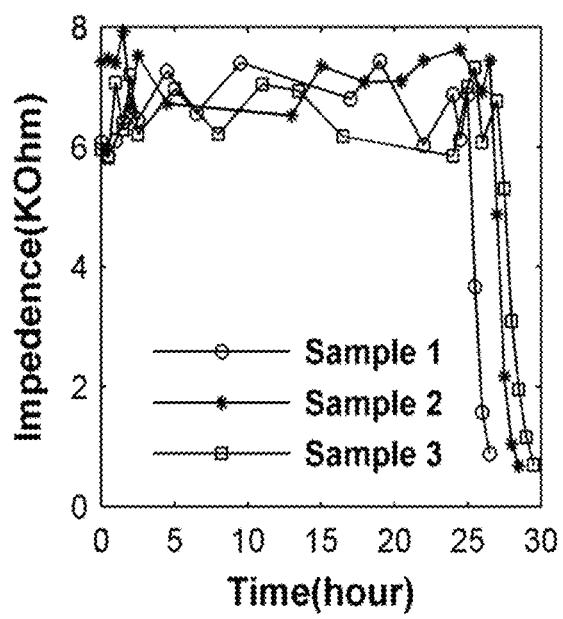

Changes in DC resistance and AC impedance of the devices were measured during substrate dissolution. Temporal change of DC resistance (with 0.1 V) and AC impedance (with 0.1 $V_{RMS}$, 1 kHz) of spiral thin film devices during the dissolution of glass substrate (2.2 mm thick, 14 mm diameter) at 37° C. FIGS. 3A and 3B show that both DC (FIG. 3A) and AC (FIG. 3B) values remained at a certain range followed by a steep decrease after one day. This change demonstrated rapid failure. These results illustrate the device performance during stages B-D in FIG. 1. Once the significant glass portion was consumed, the device collapsed and eventually short-circuited through the conductive solution. The device was largely resistive at this frequency range evidenced by the negligible contribution of reactive elements by comparing the DC and AC levels.

Although a simple metal thin film device was demonstrated in this proof-of-concept stage, silicon-based devices can be implemented to be biodegradable as described herein. Traditional substrates such as, for example, single crystal silicon and PYREX® glass are not appropriate for this application due to their extremely low dissolution rate. One practical approach is the silicon-on-insulator (SOI) structure of a glass substrate and a thin silicon layer. Therefore, biodegradable electronics with higher electron mobility are contemplated that can cover a wider bandwidth than that of biodegradable polymer devices.

Figure 4A:
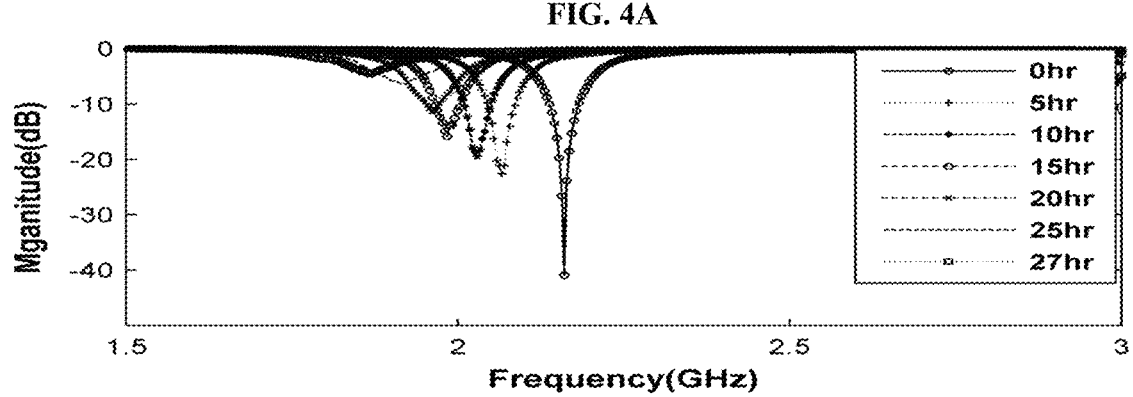
FIGS. 4A-4C depict scattering parameter response over time.
Figure 4B:
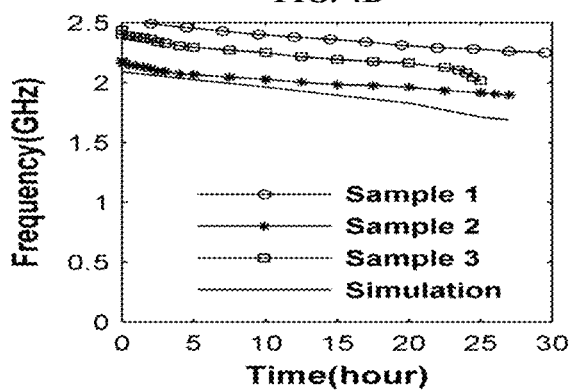

Temporal change of resonance behavior of spiral thin film devices over the course of substrate dissolution (2.2 mm thick, 14 mm diameter) was analyzed for scattering parameter (S11) spectrum, resonant frequency and peak magnitude to represent stages B-D in FIG. 1. FIG. 4A shows the temporal change of the S11 parameter over time. Upon reaching the expected lifetime (i.e., t=0 hour), the resonant peak started to shift toward the lower frequency side and became negligible (i.e., less than −5 dB) after a day (FIG. 4B). The shifting of the resonance was a result of increasing parasitic capacitance through the glass substrate ($C_v$) that was being replaced with the capacitance through the solution with a higher real dielectric constant. Additionally, this rich electrolytic solution was a lossy medium that lowered the resonance peak magnitude (FIG. 4C).

Figure 4C:
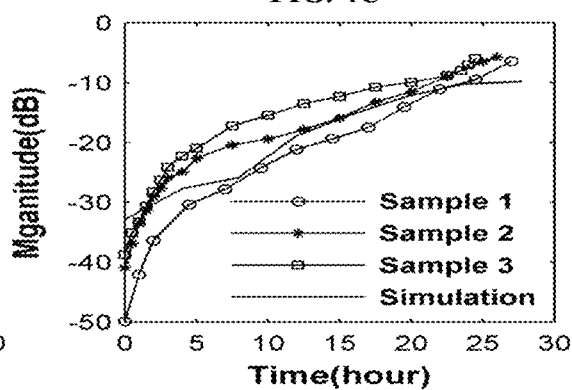

The variation in resonance frequency and peak magnitude is plotted in FIGS. 4B and 4C with respect to time. A simulation was conducted based on the varying volume of glass estimated from the weight loss observation. Both experimental and simulation data showed a similar trend and agree well taking into account discrepancies originated from the simplicity of model and the variations in the device preparation.

The resonance frequency of the exemplary device can be modified within the capabilities of those skilled in the art to vary the spiral designs and/or the size of the substrate depending on the desired needs. Operating frequencies of implantable devices can range from kHz to several GHz, depending on various factors including transmission distances, implanted depths, transmitter/receiver sizes and applications (e.g., signal transmission, power delivery, and thermal therapy). In this Example, tests were conducted in a broad frequency range to explore the feasibility of various application scenarios including simple DC (e.g., device bias), low frequency (e.g., sensing) and high frequency (e.g., RF transmission).

This Example demonstrates the rapid failure of device functionality (i.e., in one day after the estimated lifetime) built on biodegradable glass substrates over a wide frequency range, which was in good agreement with simulation based on a simple model. The inorganic biodegradable substrates of the present disclosure are more compatible with traditional device processes than other types of biodegradable substrates. Devices using the biodegradable glass substrates of the present disclosure are expected to sustain the structural integrity without compromise in device reliability during operation followed by a rapid disintegration. Therefore, the use of water-soluble glass substrates disclosed herein can be a viable approach to develop reliable biodegradable devices and systems.

Example 2

In this Example, optical devices with a glass substrate having a rapidly degradable (fast reacting) glass and a slowly degradable (slow reacting) glass were analyzed to determine functionality over time when exposed to body fluids.

A phosphate-based reactive glass served as the core material of an optical fiber. The phosphate-based glass was used to prepare the core of a light-guiding fiber, while the surrounding solution served as cladding. In this Example, the optical fiber was prepared without a slowly degradable cladding.

FIG. 5 illustrates the desired behavior of an exemplary optical device using the biodegradable glass of the present disclosure for photodynamic therapy (PDT) for use in cancer therapy, for example. Light-guiding devices (e.g., optical fibers) can deliver a localized, optimal dose of light to deep locations (e.g., several inches). Although interstitial illumination with laparoscopes is conducted as an intraoperative adjuvant treatment, it is mostly limited to single therapy that requires repeated open surgeries if the cancer recurs. With implantable biodegradable devices with percutaneous couplers, long-term monitoring and therapeutic procedures are possible during the device's lifetime (i.e., intended therapeutic period) without the need for an additional surgical procedure to remove the device.

Bioactive phosphate based fiber was prepared by grinding sodium dihydrogen phosphate monohydrate ($NaH_2PO_4H_2O$, ACS 98.0~102.0%) and calcium sulfate dibasic ($CaSO_4 \cdot 2H_2O$, ACS 98% extra pure) in a mortar for 10 minutes. The fine ground powder was mixed with phosphoric acid ($H_3PO_4$, ACS 85%) in a platinum crucible. The primary components were mixed at different weight percentage (ratio is in Table 1).

TABLE 1

| Fiber composition. | |
| --- | --- |
| Ingredient | Wt % |
| $Na_2O$ | 18.5 |
| CaO | 11.1 |
| $P_2O_5$ | 70.4 |

The crucible was then placed in an annealing furnace at 500° C. for 16~18 hours. Afterward the platinum crucible was kept in a melting furnace at 1200° C. for one hour while the melt was stirred every 15 minutes. Then the temperature of the furnace was reduced to 1100° C. and soaked for one hour. After one hour the platinum crucible was removed and fibers were pulled by hand after cooling for 2~3 minute at room temperature. Approximately 200 μm diameter fiber was pulled from the soaked and cooled liquid glass.

For determining the dissolution behavior, a sample fiber of 200 μm diameter and approximately 70 mm length was kept inside a container of phosphate buffer solution of 300 mL and completely submerged in phosphate buffer solution. The fiber was periodically taken out of the phosphate buffer solution and dried using hot dry air and weighed with a micro-balance (AE 240, Metler Toledo). Diameters at different location were measured with a micrometer (Series 293-340, Mitutoyo). To observe the dissolution behavior of the fiber at different dissolution time, an optical microscope (KH-8700, Hirox) was used to observe the cross-section.

To determine the optical properties of bulk glass, melted glass was poured into a cylindrical mold of stainless steel and annealed at 350° C. for 30 minute followed by room temperature cooling. Phosphate based glass rod measured 14 mm in diameter and 3 cm in length. Circular bioactive phosphate glass discs of approximately 3-4 mm thick were prepared by slicing a cylindrical glass rod using a low speed saw (Isomet, Buehler). The glass discs were cleaned using acetone and then mounted on aluminum holders using a thermo plastic product (Brewerbond 220, Brewer Science). The top surface of the aluminum holder was covered with a thin coating of thermo plastic. It was heated on a hot plate at 80° C. for 10 minutes, 130° C. for 10 minutes and at 200° C. for 2 hours followed by cooling. Once it reached room temperature, it was again heated to 130° C. and the glass discs were placed on top and slightly pressed followed by cooling. The bonding between the glass disc and the aluminum holder was very strong at room temperature.

The next step was polishing and grinding with automatic polisher (Tegramin30, Struers). Table 2. summarizes the process steps of grinding and polishing.

TABLE 2

Grinding and polishing steps.

| Step No | Grit Size (μm) | Polishing Agent | Force (N) | Time/Removal |
|---|---|---|---|---|
| 1 | 76 | SiC Foil | 90 | 30 seconds |
| 2 | 32.5~36 | SiC Foil | 90 | 300 μm |
| 3 | 16.7~19.7 | SiC Foil | 90 | 200 μm |
| 4 | 4.5~6.5 | SiC Foil | 90 | >3 minute |

The first step was to bring the top surface of all the mounted glass wafers to a level for which grinding was done using a SiC foil of grit size of 76 μm for 30 seconds using 90 N force. Similarly the remaining polishing steps are carried out down to the grit size of 5 micron as mentioned in the table. DP-Yellow was used as lubricant during this procedure which is an ethanol based agent. The discs were then demounted by heating the aluminum holders to a temperature of 130° C. and sliding the wafers off the holders. The wafers were then cleaned ultrasonically in 1-dodecene twice for about 15 minutes, followed by one more ultrasonication step in isopropanol for 15 minutes. They were then sprayed with isopropanol and then blown dried using high purity nitrogen gas.

The final discs after the last step were approximately 1 mm thick with a highly reflective surface. The discs were then placed inside a prism coupler (Metricon, Model 2010M) for refractive index measurement at 632 nm wavelength. Discs were also placed in a spectrophotometer (Genesis 10 uv, Thermo Scientific) to measure transmission and absorption coefficient. Measurements were carried out from 190 nm to 1100 nm at 1 nm step size.

For refractive index measurement of phosphate buffer solution (PBS), ellipsometry technique was used. Sample solutions were placed in a known refractive index dish and 5 ml of solution was placed inside dish to create a thin film of solution and ellipsometer was scanned from 600 nm to 700 nm wavelength and real part of refractive index was measured.

To determine fiber transmission properties, pulled fibers of 200 μm diameter were used for propagation loss measurement. A fiber of approximately 150 mm length was taken and both ends were cut sharply with an optical slicer and one end was aligned to the output of the laser source (632 nm, 0.5 mW He—Ne polarized, Edmund Optics). This wavelength is used for one of the most common photosensitizer (e.g. protoporphyrin). The other end was placed inside the collection chamber of power meter (Model 2935C, Newport) to measure transmitted power was measured. Afterward, 25 mm fiber from the power meter end was repeatedly cut sharply and again transmitted power was measured. Subsequent power reading was calculated and propagation loss was measured in dB/km using equation 1 where $P_1$ is the output power at length $L_1$ and $P_2$ is the output power at length $L_2$ respectively, while $L_1$ is longer than $L_2$.

$$P_{loss} = \frac{-10\log_{10}(P_1/P_2)}{L_1 - L_2} \quad \text{(equation 1)}$$

Fibers of 200 μm diameter and 100 mm length were placed inside a black sample container (75×40×100 mm³). The two ends of fiber were cut sharply. One end was aligned to laser source output, while the other being inside the collection chamber of optical power meter. The sample container was filled with 300 mL of phosphate buffer solution (PBS, pH 7.4, Sigma Aldrich) at room temperature and transmitted power was periodically measured until the fiber completely dissolved (approximately 10 days).

An optical simulation software (Mode Solution, Lumerical) was used for the simulation of transmission through fiber. The starting core diameter was 200 μm which decreased with respect to time as the fiber dissolved. The change of diameter was taken from experimental data obtained from the dissolution experiment. The surrounding PBS was considered as a cladding layer with constant refractive index. Two ports were placed at two ends of fiber and scattering parameter S21 was calculated which reflected the transmitted power. A conceptual diagram is shown in FIG. 6.

Figure 7:
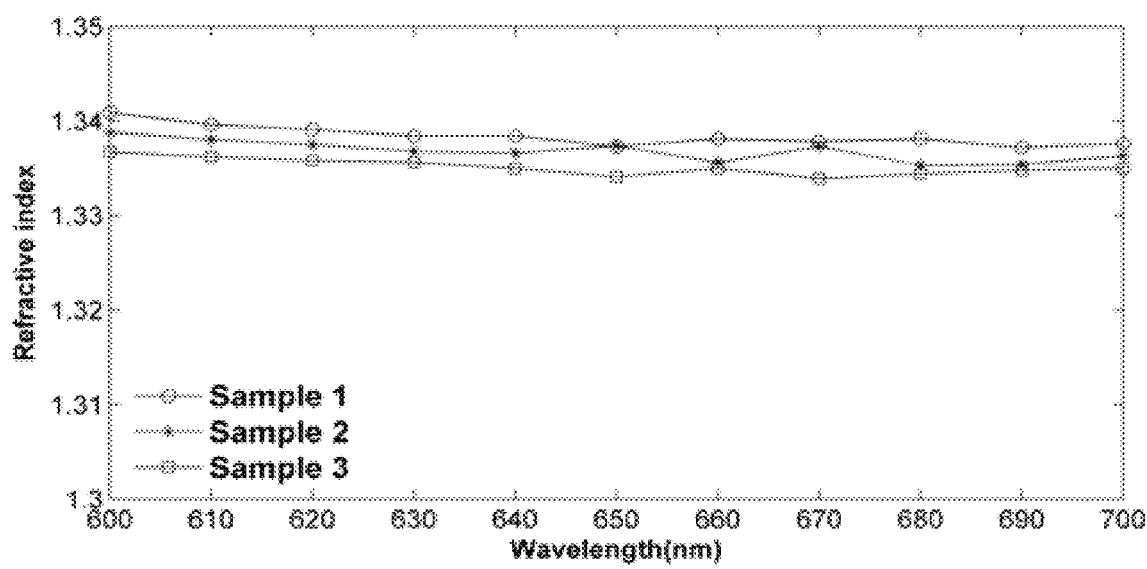
FIG. 7 depicts the refractive index of phosphate buffer solution measured from 600 nm to 700 nm. Standard deviation of 0.22%.

The refractive index of phosphate buffer solution measured using ellipsometry was approximately 1.34. FIG. 7 shows the refractive index measured from 600 nm to 700 nm. At 632 nm the refractive index for phosphate buffer was approximately 1.3369 with a standard deviation of 0.22%.

Refractive index of phosphate-based glass measured with a prism coupler was 1.5225 (standard deviation=0.02%; n=3). This indicates the glass can be used as a light guiding fiber submerged in phosphate buffer solution as the refractive index was higher than that of the solution to support multiple propagation modes and a high numerical aperture 0.72 based on the equation 2 where NA is numerical aperture, n is the refractive index of the medium with light source, $n_1$ is the refractive index of core and $n_2$ is the refractive index of cladding. High numerical aperture essentially secures the insertion of a large portion of the light incident while multi-modes ensure the availability of higher transmitted power per wavelength.

$$NA = n \sin\theta = \sqrt{n_1^2 - n_2^2} \quad \text{(equation 2)}$$

Figure 8A:
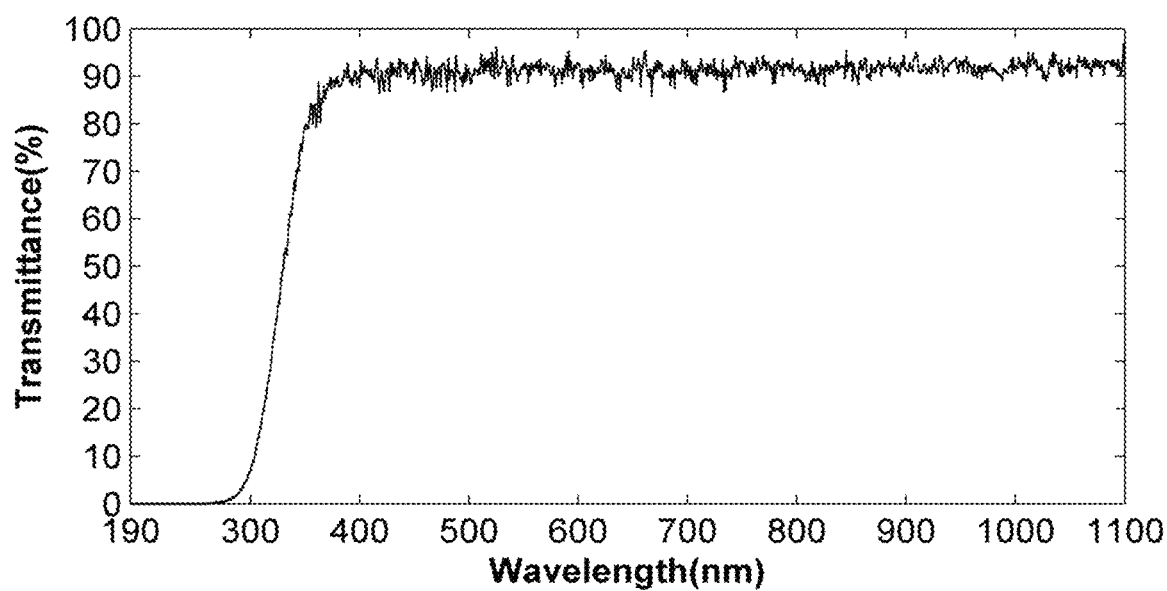
FIG. 8A depicts the transmission spectra of bulk phosphate glass (Thickness=1 mm).
Figure 8B:
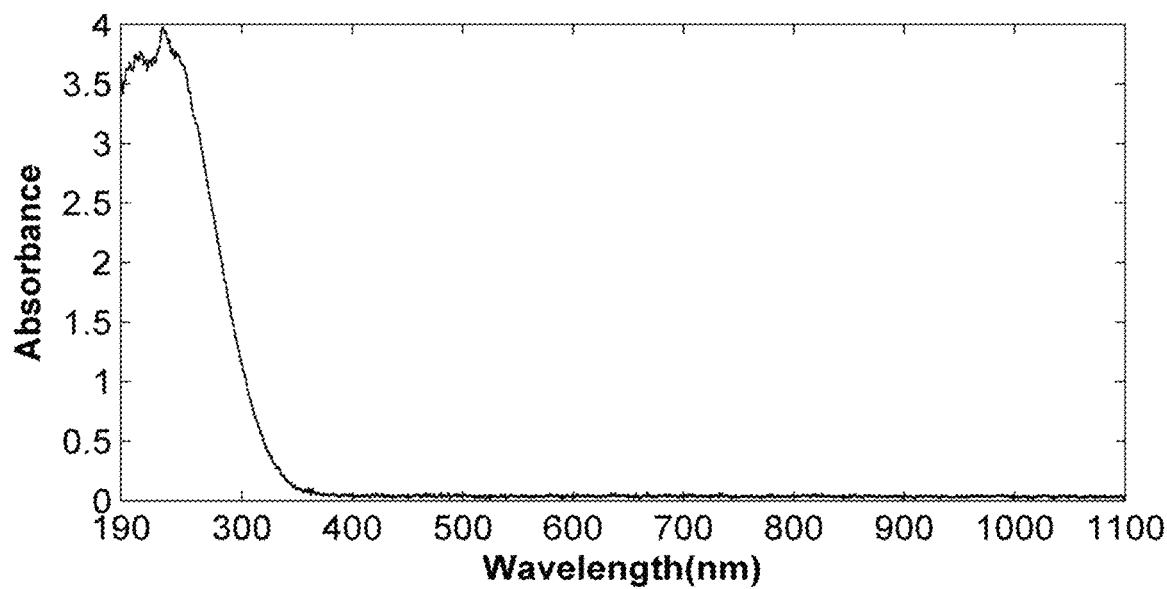
FIG. 8B depicts the absorption spectra of bulk phosphate glass (Thickness=1 mm).

FIGS. 8A and 8B show the transmission (FIG. 8A) and absorption (FIG. 8B) spectra. The transmission and absorption are defined as shown in equations 3 and 4 where $I_o$ is blank reference intensity and I is sample intensity respectively.

$$T = (I/I_o) * 100 [\%] \quad \text{(equation 3)}$$

$$A = 2 - \log_{10}(\% \, T) \, [\text{unit-less}] \quad \text{(equation 4)}$$

Transmission was initially low and rises sharply at the UV range reaching approximately 90 percent while at 400 nm. After that a minor fluctuation was observed in the transmission spectra while the average stayed at approximately 90 percent. An opposite response was observed in the absorbance. At near ultraviolet region, absorbance was high and dropped to a very low value near 350 nm. This result indicates that the proposed glass fiber of this composition can effectively deliver the expected wavelength (632 nm) inside the body during therapeutic procedures.

As summarized in Table 3, the optical fiber had a propagation loss of approximately 14.5 dB/m at 632 nm wavelength. Although propagation loss varied but with low standard deviation, it may have resulted from manmade inconsistency during cutting of the fiber or incoherent dispersion from the receiving end due to unseen fiber cross-section. This loss was significantly high compared to those of conventional silica based fibers (usually less than 10 dB/km) used in telecommunication. However, since the required depth of implantation for therapy is only a couple of inches deep, this loss is not problematic for the proposed PDT applications.

TABLE 3

Propagation loss.

| Sample | Average (dB/m) | Standard Deviation (dB/m) | No of Measurements |
| --- | --- | --- | --- |
| 1 | 14.19 | 0.32 | 5 |
| 2 | 14.79 | 0.21 | 4 |
| 3 | 14.13 | 0.28 | 4 |

Figure 9:
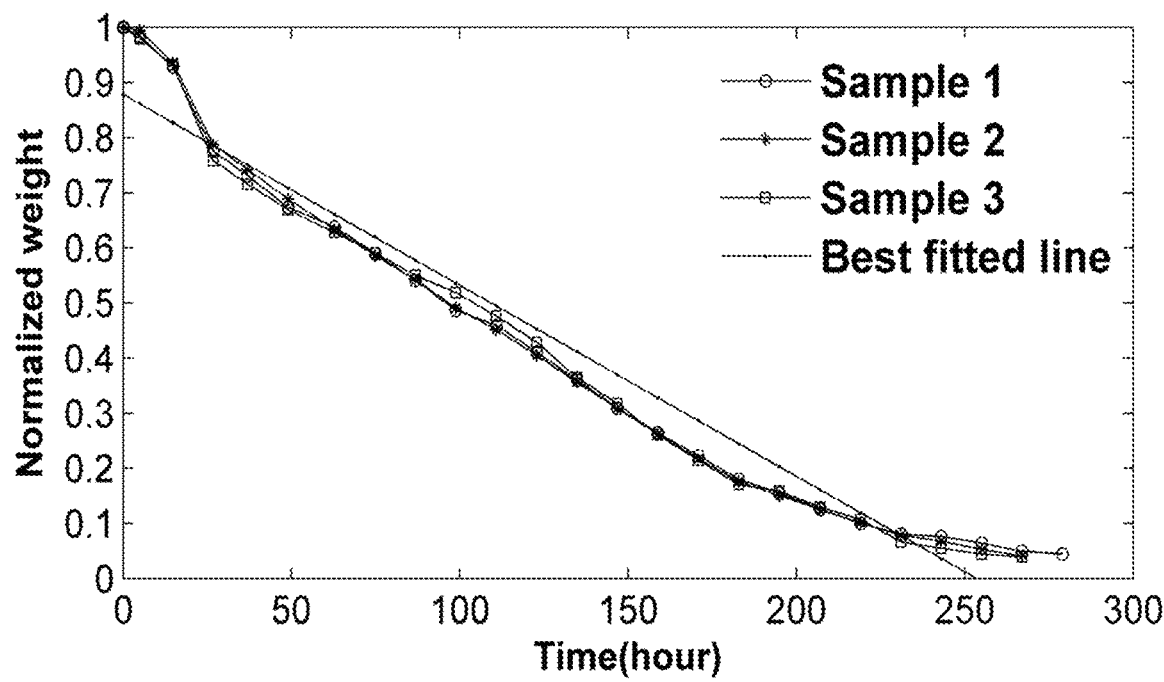
FIG. 9 depicts the dissolution of a phosphate fiber (diameter 200 μm, length: 70 mm) at 21° C.

Dissolution behavior of phosphate glass fiber is shown in FIG. 9. Dissolution rate depended on several factors such as mechanism of reacting layer formation, exposed surface area, composition of phosphate buffer solution and temperature. The dissolution rate was approximately 3.5 mg/hour with the original surface area approximately 0.43 cm2. This rate is comparable with those of other phosphate-based glass material which are within the range of approximately 4 mg/hour.

Figure 10:
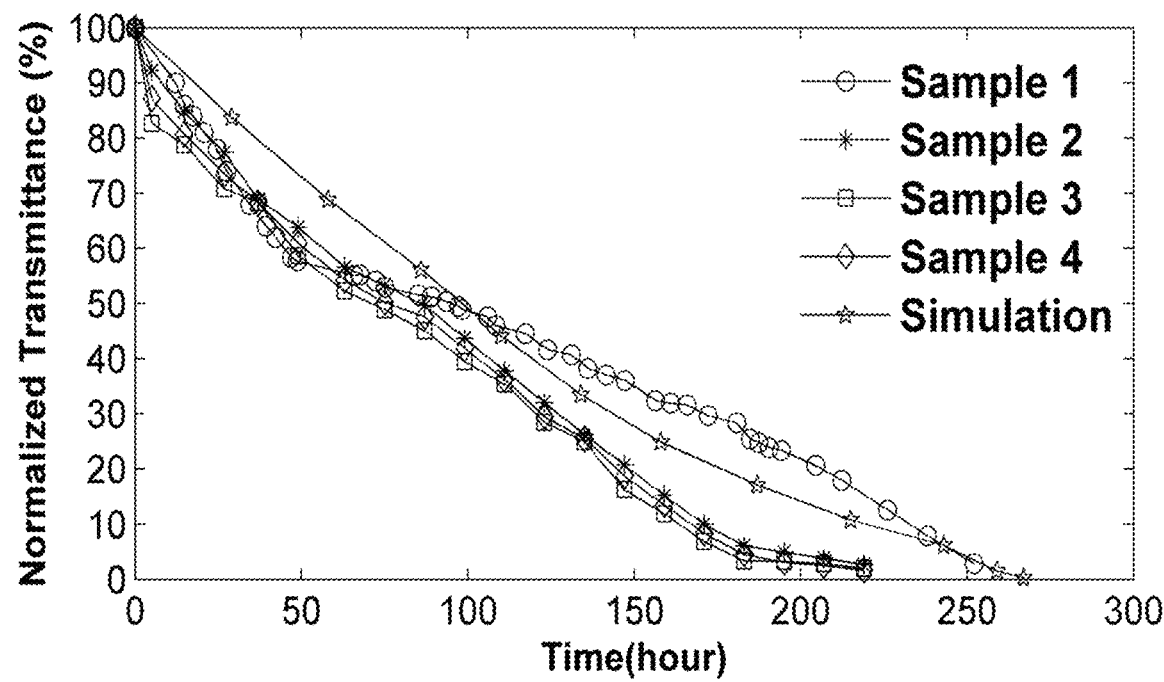
FIG. 10 depicts the transmission change during fiber (diameter 20 μm, length: 100 mm) dissolution in PBS at 21° C.

Transmission through the phosphate-based fiber over the course of dissolution time is plotted in FIG. 10. This optical fiber (without a slowly degradable glass cladding) demonstrates stages 3-4 of FIG. 5B showing the rapid intended failure. The decrease in transmission was mainly due to the reduction of fiber (i.e., cross-sectional area) during dissolution. In addition, the reaction layer on the surface had a different refractive index, while the phosphate buffer which acts as cladding also had a varying refractive index over time due to ionic accumulation. Other factors also influence this change in transmission including porosity and surface roughness of reaction layer.

Simulation result of transmission during dissolution is shown in FIG. 10. The simulation was based on the separately measured diameter over time with different fiber samples. To utilize this data in simulation, diameters were converted to equivalent time period immersed in PBS. In simulation, the diameter was the only variable considered while the refractive indexes of fiber and phosphate buffer solution remained constant which is different in a real situation. Also the simulation was done only within the portion of fiber submerged in phosphate buffer, while in the experimental procedure there are two distal ends that were not immersed in PBS for laser sourcing and detection. Potential high scattering loss at this area where unchanged fiber and dissolved fiber meets was not reflected in the simulation. Also due to the limitation of modeling software, the surface roughness of reaction layer was not considered. Overall, the experimental and simulation results agreed well despite the simplicity of the simulation model and various deviations from the real experiment.

Figure 11:
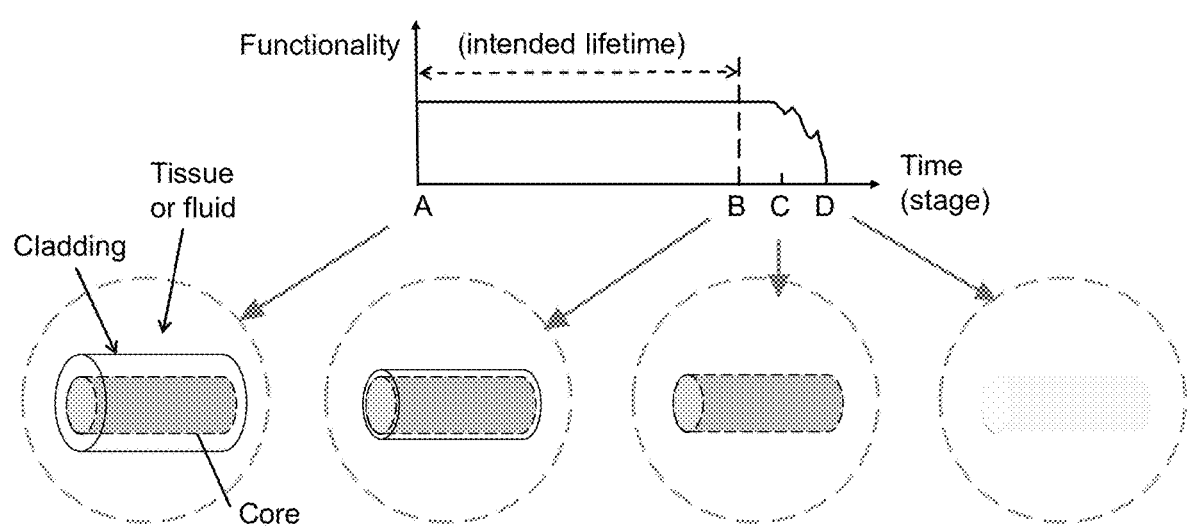
FIG. 11 depicts stages A-D of dissolution of the optical fiber.

These results demonstrate viability for delivering light using a biodegradable optical fiber for a certain operational lifetime before structural disintegration of the device. FIG. 11 depicts stages A-D of dissolution of the optical fiber. At stage A, the optical fiber with a core of rapidly degrading glass is surrounded by a cladding of slowly degrading glass and positioned within a tissue or fluid. Stage B depicts reduction of the thickness of the cladding (compared to the thickness of the cladding at Stage A). At Stage C, the cladding has degraded to expose surfaces of the rapidly degrading glass that formed the core of the optical fiber and the functionality of the optical device begins to decline. At Stage D, the rapidly degrading glass dissolves and the optical device ceases to function. Potential applications of the optical devices include photodynamic therapy (PDT) for deep-seated inoperable tumors and infected tissues without needing surgical procedures for removing the optical fibers.

Photodynamic therapy (PDT) is an emerging therapeutic modality for cancers and infectious diseases based on the light-induced cell death. Light-activated reactive oxygen species (ROS) destroys the tissue with three required ingredients which are light (mostly visible range), oxygen dependent photosensitizer (mostly porphyrin-based) and tissue oxygen. This approach is particularly promising because of the use of non-ionizing radiation (visible to near IR), minimally invasive in nature, highly portable and low cost procedure. However several challenging technical issues exist for PDT to become one of mainstream cancer treatments including its limited application to surface treatment, highest possible single dose of light and photosensitizer per outpatient visit (as opposed to low dose repetitive interventional therapy) and low efficiency for large solid tumors with hypoxic environment owing to oxygen unavailability. Accordingly, an emerging approach has been identified as a new direction in PDT development which focuses on delivering the optimal light and photosensitizer separately over a period especially for brain tumors for which this therapeutic modality is more efficient appropriate.

Example 3

In this Example, an implantable biomedical device with an inorganic substrate having a rapidly degradable (fast reacting) glass but without a slowly degradable (slow reacting) glass was analyzed to monitor the intervertebral pressure in the lumbar region of the human body.

In this Example, biodegradable borate glass ($B_2O_3$, 69.2 wt % and $Na_2O$, 30.8 wt %) was used as the main structural material to develop the pressure sensor. Over the course of its degradation, the glass completely dissolves inside the body leaving no hydroxyapatite residues due to absence of calcium ingredient. The rate of degradation of this borate glasses is higher than that of borate glasses containing silicates. In this proof-of-concept stage, there was no protective slow-reaction material coated on the glass substrate and hence a rapid degradation of the device structure was observed. Therefore, this Example was focused on demonstrating the working of the device structure for a short period of time depicted between stages B to C in FIG. 1. The biodegradable glass substrates were prepared manually in form of discs. It is contemplated that they can be mass-produced industrially in a more refined manner.

A polydimethyl siloxane (PDMS) elastomer (Sylgard 184, Dow Corning) was used as the elastic insulator between the electrodes of the capacitor. PDMS commonly known as silicone, is an elastic, inexpensive polymer widely used in various lab-on-chip (LOC) platforms due to its advantages of biocompatibility, elasticity and processability for device fabrication. PDMS sheets can be easily prepared by spin coating processes. PDMS also has an excellent property to bond to itself and also other materials creating water-tight seals. It is known that PDMS retains its bulk elastic property when the sample has at least 200 μm thickness. This is the proper range of dimension for sensor applications for biomechanical pressure monitoring.

All the dissolution tests performed in this Example were conducted in phosphate buffer saline (PBS) solution (pH 7.4, Sigma-Aldrich) and the temperature of the solution was kept at 37° C. using a hot plate and incubator (Heratherm Incubator, Thermo Scientific). PBS was used to simulate the body environment because the osmolarity and ion concentration resembles those of the body fluids.

Mean and standard deviation values of the upper vertebral width (UVW) or lower vertebral width (LVW) and upper vertebral depth (UVD) or lower vertebral depth (LVD) of L4 and L5 were obtained from a published study of 126 adults patients with low back pain and varying degrees of disc degeneration but without abnormalities or other major spinal pathologies including spondylolisthesis and disc space collapse, etc. The dimension of intervertebral disc space geometric is also an important factor to design the thickness of the pressure sensor. The normal lumbar disc space between third-fourth and fourth-fifth lumbar discs were from published measurements obtained by magnetic resonance imaging (MRI) in total 178 adult patients having lower back pain, but no other critical spinal pathological conditions. Using the width and depth measurements, the diameter of the sensor device was designed to be 14 mm so that it can be placed in the central region of the vertebral body. Using the minimum distance between the discs, the pressure sensor was made by using two glass substrates, each with thickness of 2.8 mm making the total thickness of the sensor device approximately 5.6 mm. The thickness of the sensor can be altered depending on the particular use and placement position inside the disc area.

A circular electrode with 8 mm diameter was prepared on the center of the glass disc having 14 mm diameter. This allowed for a 3 mm distance between the edge of the glass substrate and the electrode. The PDMS elastomer used in this Example had a dielectric constant of approximately 2.7 at 100 Hz-100 KHz range. Circular PDMS sheets of diameter 16 mm were used to entirely cover the glass substrate to ensure water-sealing. The thickness of the elastomer was approximately 250 μm to retain its bulk elasticity when the external compressive force was removed. The parallel-plate capacitor structure produced a capacitance of 7.2 pF at 1 KHz based on equation 5 (where f is the frequency of the operation voltage) without compressive pressure. Hence with each biodegradable glass discs being 14 mm diameter, 2.8 mm thick, circular electrode diameter of 8 mm and PDMS elastomer thickness approximately 250 μm and diameter of 16 mm, the dimension of the final sensor device was 16 mm diameter and approximately 5.6 mm thick.

$$Z = 1/2\pi f C \quad \text{(equation 5)}$$

Borate glass substrates were prepared by melting 99.5% anhydrous sodium tetra borate in a platinum crucible at 1000° C. for 30 minutes. The molten glass was then immediately poured in stainless steel molds having dimensions 14 mm diameter and 30 mm height. The mold was annealed at 450° C. for 30 minutes and then kept inside melting chamber overnight for slow cooling with the chamber turned off. The glass rods (14 mm diameter and 30 mm long) were then sliced using a circular low-speed saw (Isomet, Buehler) to form glass substrates of approximately 2.8 mm thickness.

The glass discs were then cleaned with acetone and mounted on aluminum holders using a thermoplastic adhesive (Brewer Bond, Brewer Science). They were clamped into the specimen holder and polished using silicon carbide foils (180 μm to 1200 μm grit sizes, Struers) followed by diamond polishing using diamond media (DP spray P, Struers) in the automatic polisher machine (Tegramin 30, Struers). After polishing, the discs were demounted and cleaned ultrasonically in dodecene and then isopropanol each for 15 minutes. It was followed by wiping the discs using microfiber cloth (TX 1009, Alpha Wipe) and then spraying isopropanol on it. Finally it was blown dried using compressed nitrogen gas. The electrodes of the parallel plate capacitor (8 mm diameter) were prepared with a gold layer (120 nm thick) deposited by sputtering using a flash coater (E5400, Bio-Rad) and patterned using a polymer shadow mask on the glass substrate during deposition.

The elastomeric insulator was fabricated using PDMS. It is a two part mixture, where the base and the curing agent were mixed thoroughly in the ratio of 10:1 by weight. It was then degassed using a vacuum chamber for 30 minutes. The degassed mixture was spin coated with a spin coater (WS-400B-6NPV/LITE, Laurell) on a circular acrylic sheet (Optix, Plaskolite Inc.) of 8.5 cm diameter and 2 mm thickness. A coating at 400 rpm, 50 rpm$^2$ acceleration for 30 seconds followed by curing at room temperature for 48 hours. The resulting thickness of the PDMS obtained was approximately 250 μm. It was cut into circular pieces of 16 mm diameter with a hollow metal puncher. Prior to bonding, it was ultrasonically cleaned with ethanol for 5 minutes and then dried using compressed air.

Figure 12:
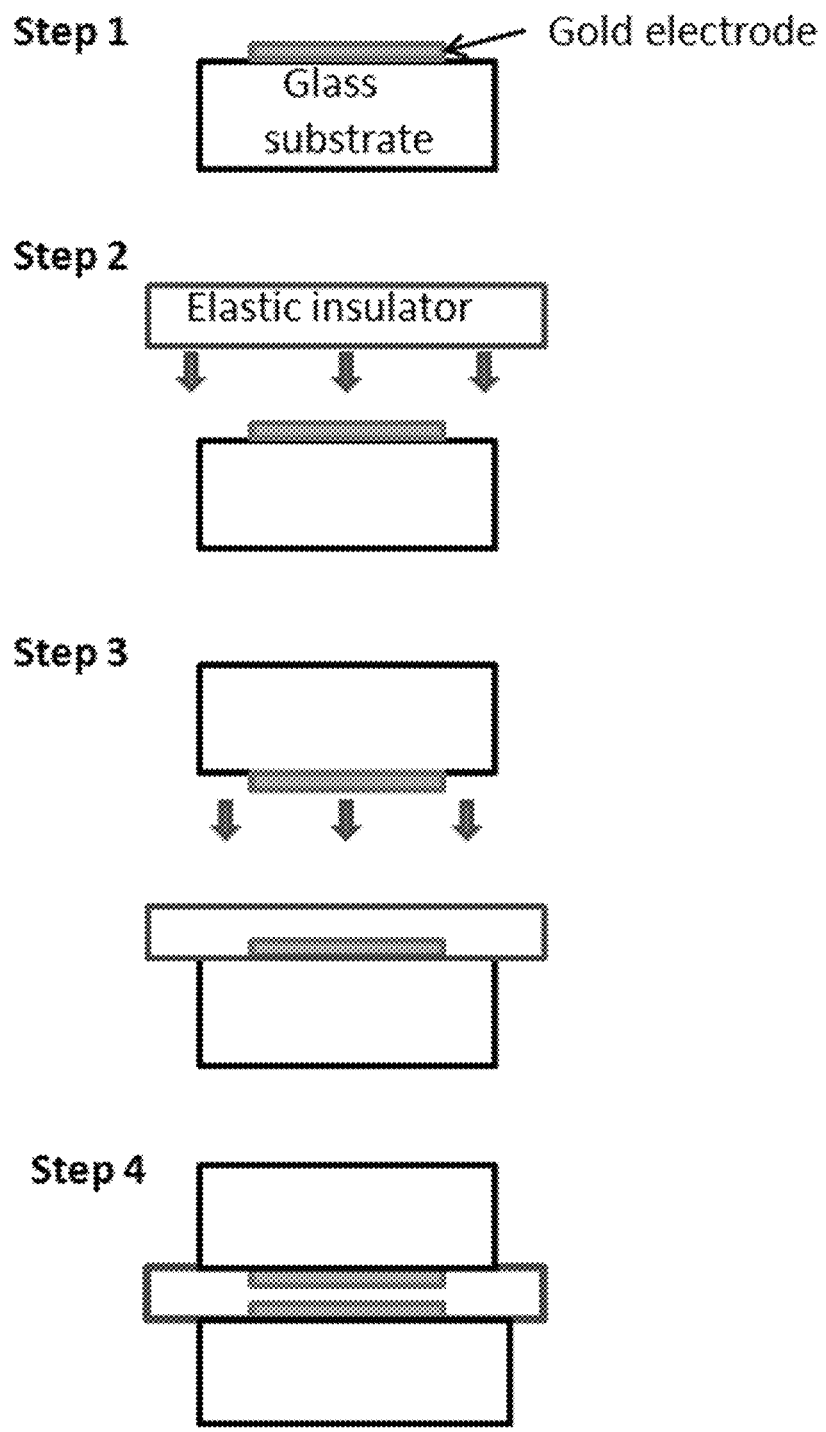
FIG. 12 illustrates the fabrication process flow in a cross-sectional view of the device.

One side of the PDMS insulator and one side of the glass disc where the electrode was deposited were treated by oxygen plasma with a reactive ion etcher (PE-200, Plasma System). Then the plasma-treated surfaces of both insulator and glass substrate were irreversibly bonded to each other. Then the other glass disc and the other surface of the previously bonded insulator were bonded through the same procedure. FIG. 12 illustrates the fabrication process flow in a cross-sectional view of the device. Step 1 of FIG. 12 shows gold electrode deposited on glass disc; Step 2 shows bonding elastomer spacer to glass; Step 3 shows bonding the other glass having electrode to the other structure; and Step 4 shows the final device structure (before coax cable connection).

Figure 13:
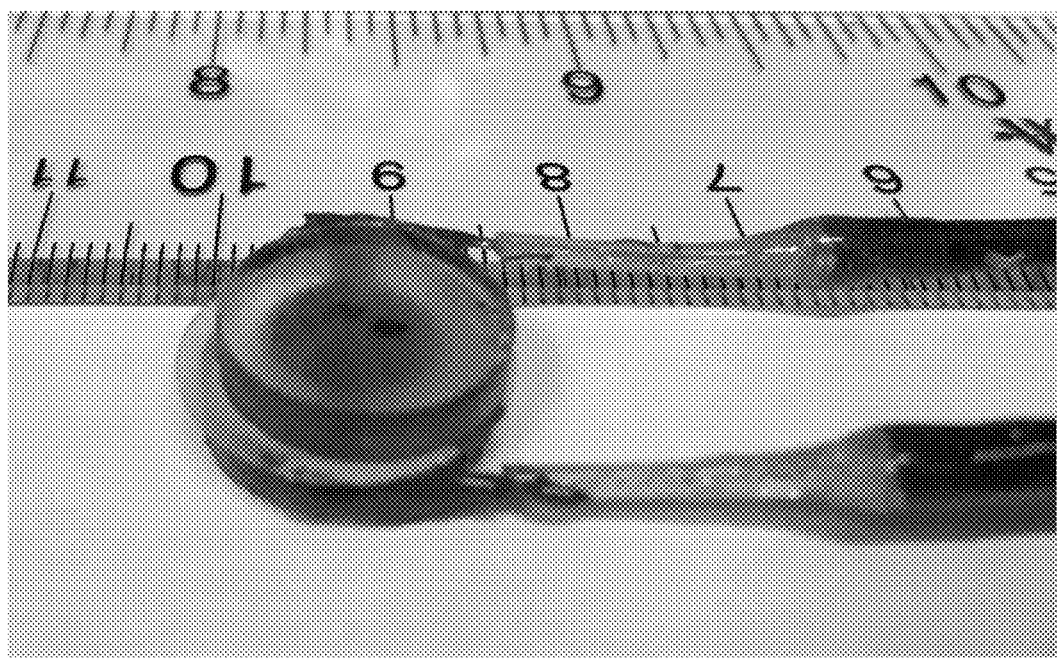
FIG. 13 is a photograph of the final assembled device as prepared in the illustration of FIG. 12.

Coaxial cables were then connected to the trace of the electrodes formed over the side walls of the glass substrates using a silver paste (SEC1233, ResinLab). To give mechanical strength and passivation against solution to the connected portion, an epoxy and encapsulant (JB Weld Epoxy and Dow Corning RTV Silicone) respectively were applied. FIG. 13 is a photograph of the final assembled device.

To monitor the AC impedance levels during the course of device operation, the device was connected by shielded coaxial cables to an electrochemical potentiostat (Femtostat, Gamry). For the purpose of calibrating the biosensor device, a commercial load cell (LC302, Omega), capable of measuring load up to 500 lbs was used with its display meter (DP25BS-A, Omega) to read externally applied compressive load on the device.

A precision vise (EVSD-S60, Interstate) was used to manually apply external compressive pressure on the device to mimic the spinal loading mechanism after implantation. The device and the commercial load cell were placed between the lower jaw and the upper jaw of the vise. The load cell was used to read the magnitude of the load applied manually by lowering the upper jaw of the vise. The change in impedance value corresponding to pressure applied was converted to the load.

To determine the compressive modulus of the PDMS elastomeric insulator material, the precision vise along with the load cell and a digital microscope (KH-8700, Hirox) were used. Optical images were recorded to measure the change of PDMS thickness with the optical microscope to measure the strain developed in the PDMS material. Hence the values of applied compressive stress and corresponding value of strain on the elastomeric insulator enabled estimation of its compressive modulus.

The glass substrate dissolution test was done in 2 L of phosphate buffer solution kept at 37° C. and stirred by a magnetic bar rotated at 60 rpm. The dissolution test was performed to determine the weight loss rate, thickness reduction rate and diameter reduction rate of the disc-shaped glass substrates. The weight loss rate of the glass allows for determining how long it will take for the substrate to totally dissolve inside the body. The thickness and diameter reduction rates of the glass substrates allows for determining the time duration for which the device can maintain its structural integrity or in other word its lifetime before it collapses and reaches 'sudden failure'.

Figure 14:
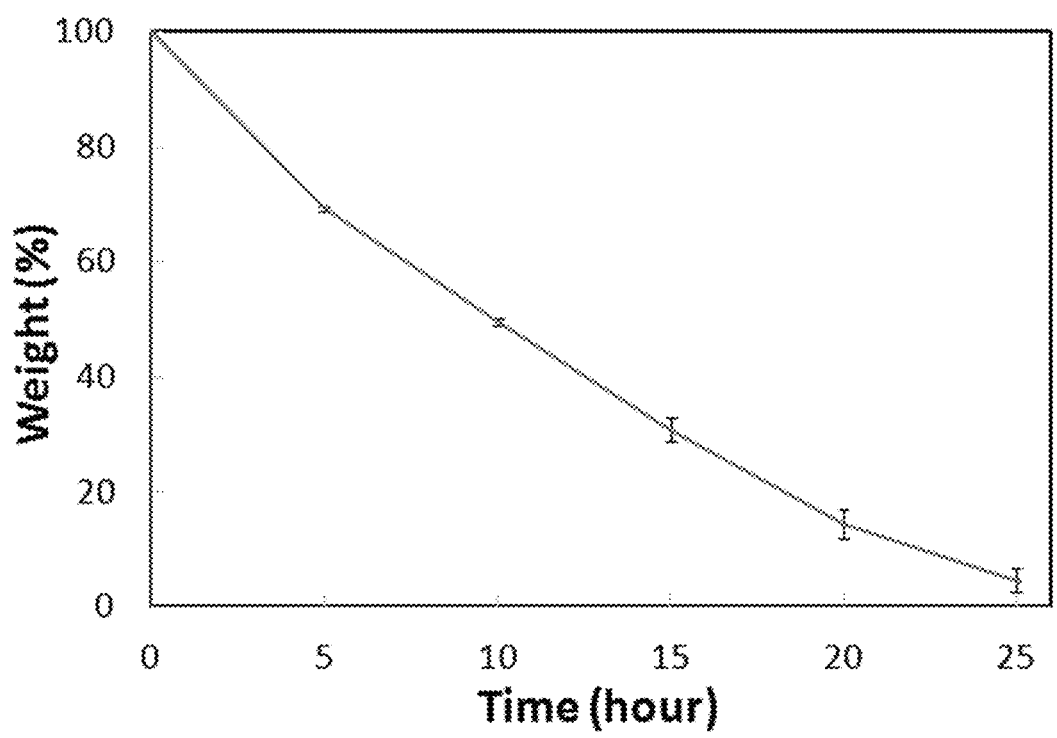
FIG. 14 depicts the dissolution behavior of bare glass substrates (2.7 mm thick, 14 mm diameter, no coating/encapsulation) in phosphate buffer saline solution (pH 7.4 at 37° C.). (Weight % vs. time).

FIG. 14 shows the linear weight loss rate of the glass substrates. It took approximately 25 hours for each glass substrate weighing approximately 1 g to be totally dissolved in the solution. Since these samples did not have any slow-reaction layer, the time duration was not an indication regarding how long the device could remain functional (FIG. 1 stage A-stage B), rather it indicated how long time the glass will take to get totally dissolved inside the body (FIG. 1 stage B-stage D).

Figure 15:
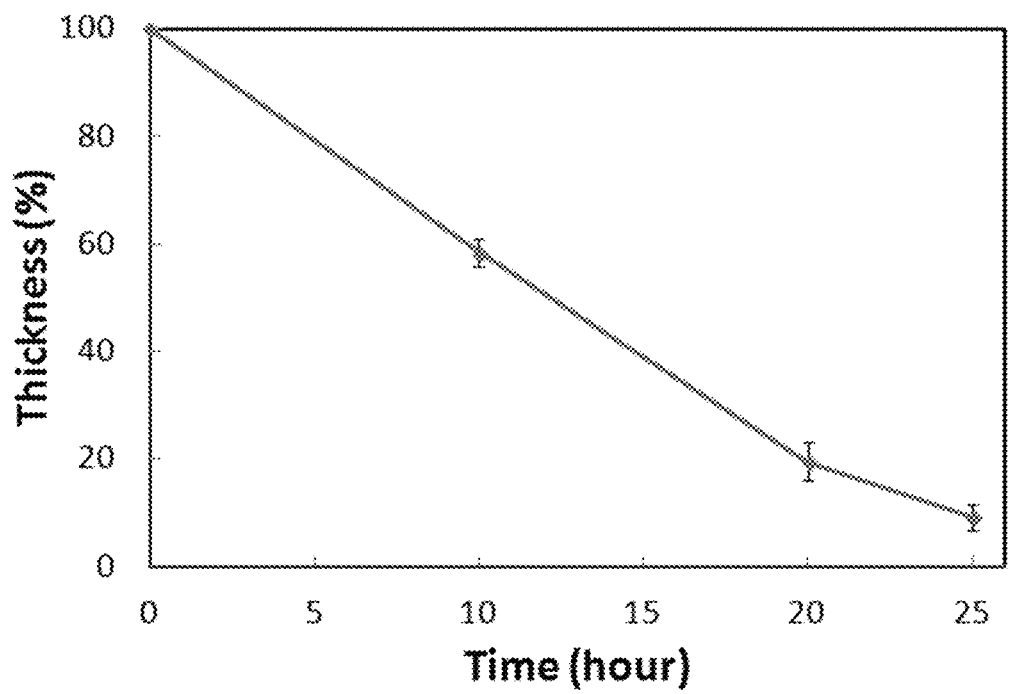
FIG. 15 depicts the dissolution behavior of bare glass substrates (2.7 mm thick, 14 mm diameter, no coating/encapsulation) in phosphate buffer saline solution (pH 7.4 at 37° C.). (Thickness % vs. time).
Figure 16:
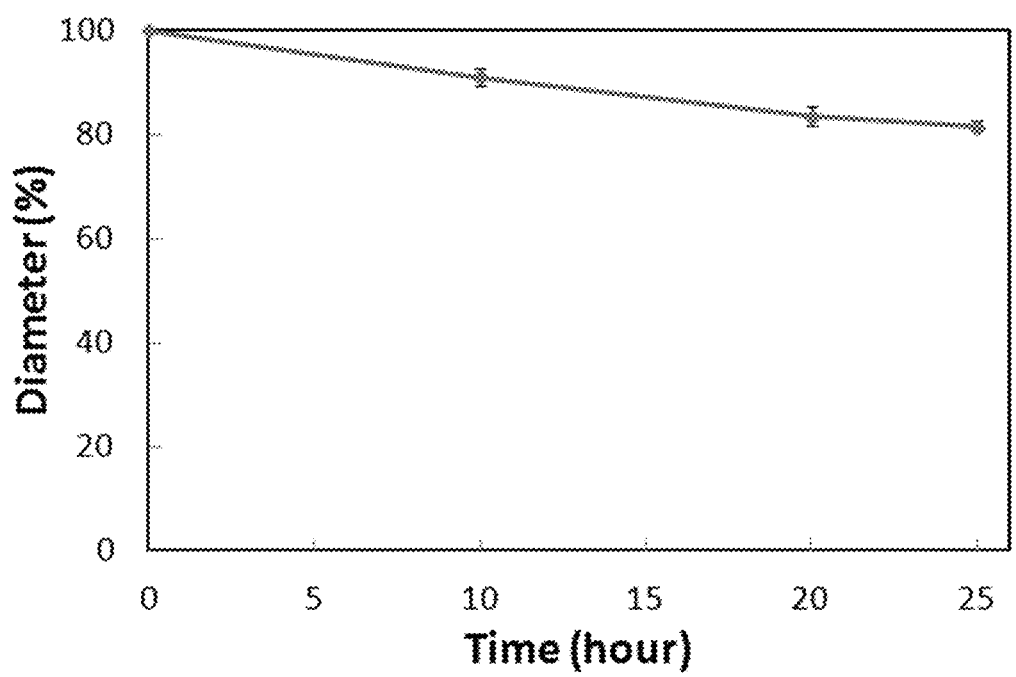
FIG. 16 depicts the dissolution behavior of bare glass substrates (2.7 mm thick, 14 mm diameter, no coating/encapsulation) in phosphate buffer saline solution (pH 7.4 at 37° C.). (Diameter % vs. time).
Figure 17A:
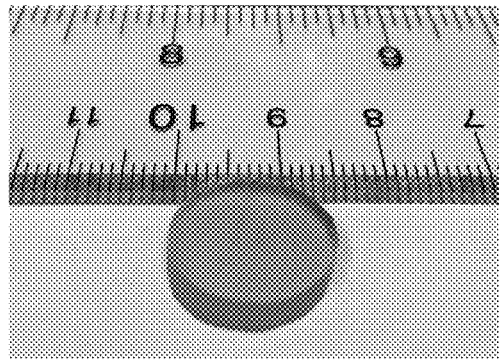
FIGS. 17A-17E are photographs of glass substrates taken at various stages of dissolution i.e., at (FIG. 17A) original, (FIG. 17B) 10 hours, (FIG. 17C) 20 hours, (FIG. 17D) 25 hours and (FIG. 17E) 26 hours in PBS (pH 7.4, 37° C. respectively).
Figure 17B:
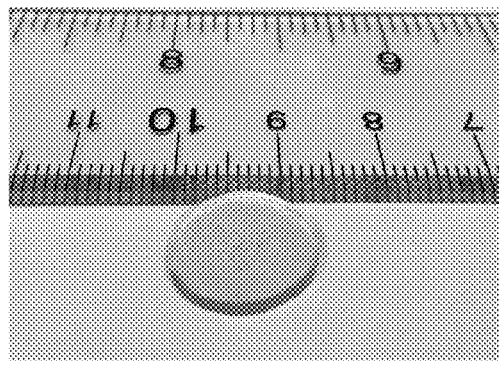
Figure 17C:
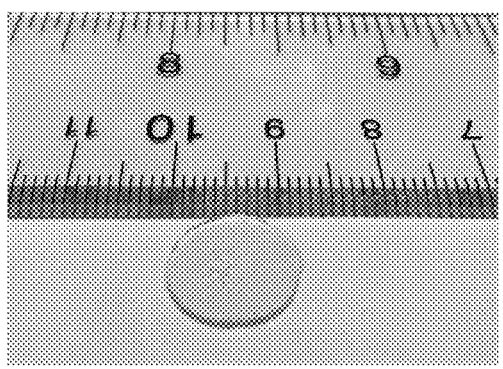
Figure 17D:
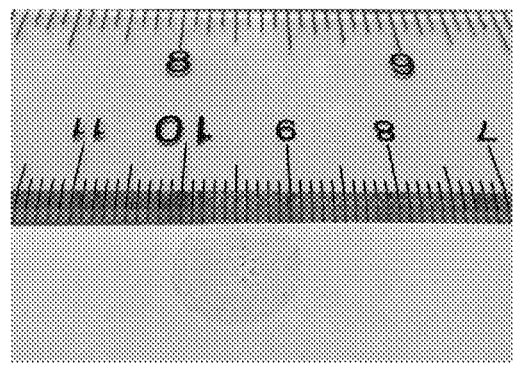
Figure 17E:
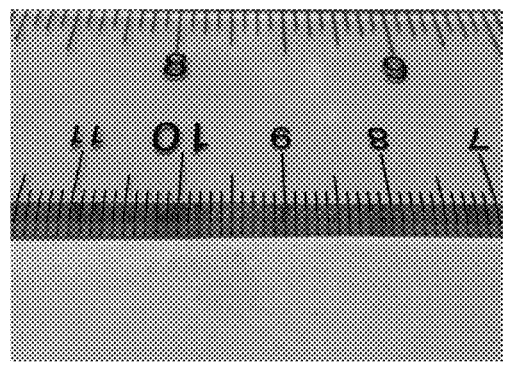

FIG. 15 and FIG. 16 show the linear thickness reduction rate of each glass substrate and the diameter reduction rate, respectively. The thickness reduction rate was higher than the diameter reduction rate because of a larger surface area of the top and bottom of the glass substrate being exposed to solution than the sides. FIGS. 17A-17E shows photographic images of glass substrates during course of dissolution at 0 hour (FIG. 17A), 10 hour (FIG. 17B), 20 hour (FIG. 17C), 25 hour (FIG. 17D) and 26 hour (FIG. 17E) after immersion in solution, respectively. This rate can be controlled by modifying the glass composition with higher percentage of silicate to achieve lower rates.

PDMS was used as the elastomeric insulator for the capacitive sensor. Factors determining the mechanical property of PDMS include the base to agent mixing ratio, curing temperature and thickness. In the sensor design, having higher compressive modulus value of PDMS is preferred in order to accomplish the wider dynamic range of applied pressure. The elastic modulus increased with increase in base-to-agent ratio up to 10:1 by weight, after which it decreased with higher ratio.

Figure 18:
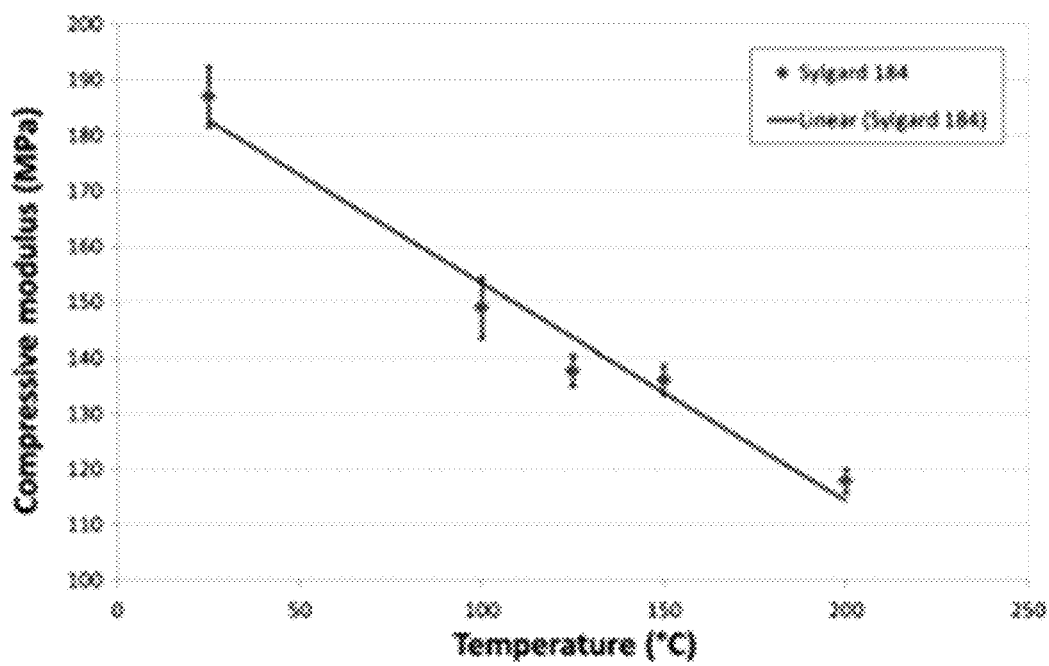
FIG. 18 depicts the compressive modulus of PDMS elastomer vs. curing temperature for sample preparation according to ASTM D575-91 standards.

Curing temperature of spin coated PDMS also effected the compressive modulus. Curing at room temperature (i.e. 25° C.) for 48 hours produced the highest compressive modulus compared to higher curing temperatures as shown in FIG. 18.

Although quantitative analysis of adhesion between the acrylic sheet and PDMS was not conducted by a peel test, it was observed that cured PDMS sheets were easily peeled off of the acrylic substrate without the need for an additional sacrificial layer. Hence, an acrylic sheet provides an excellent substitute as substrate for spin-coating PDMS due to its low adhesion property to PDMS.

PDMS samples as thin as 200 μm can retain their shape memory with repeated compressive force application. The thickness of the PDMS after spin coating depends on the rpm, acceleration, spin duration, amount of PDMS poured and also surface property and area of substrate used. In this Example, the rpm was varied to obtain the desired PDMS thickness of approximately 250 μm.

Figure 19:
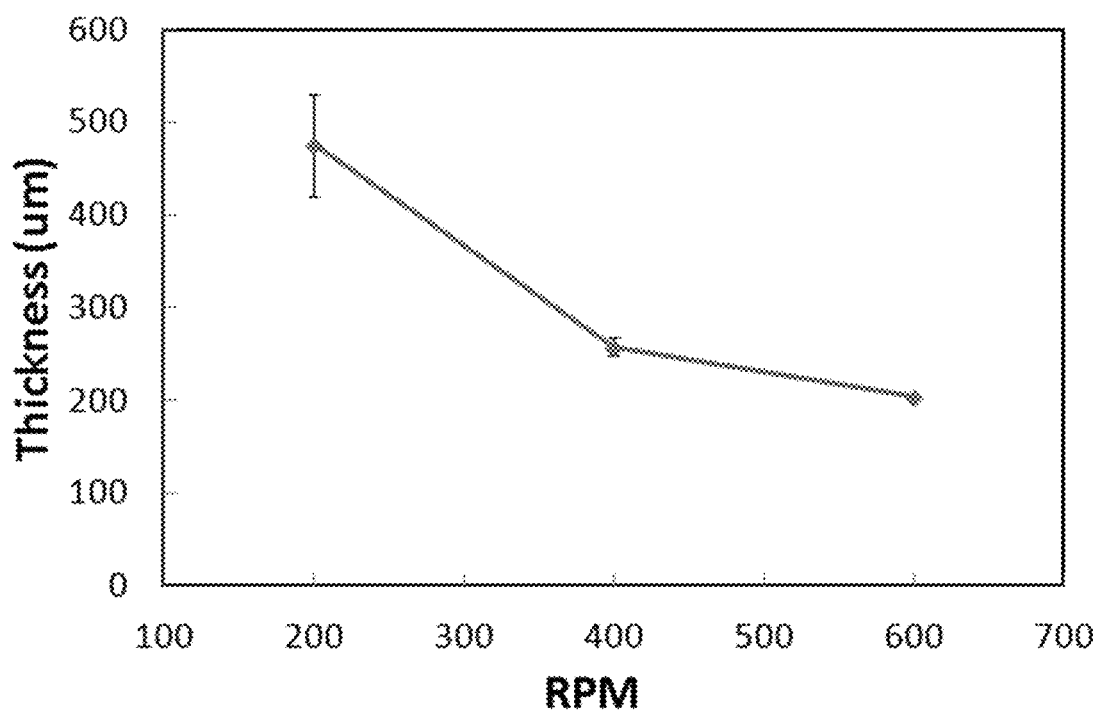
FIG. 19 depicts the variation of thickness of PDMS elastomer vs. spin speed for preparation.

Mechanical characterization was conducted to determine the compressive modulus (CM) of the PDMS elastomer. The compressive stress-strain plot allowed for determining the dynamic range of the pressure sensor that is the linear region of the plot. This indicates that the sensor had repeatability in that linear range, based on the elastomer's shape-retention capability within that pressure range. FIG. 19 indicates that the PDMS thickness of approximately 250 μm was obtained at 400 rpm for 30 sec spin-coat time, base to agent mixing ratio of 10:1 by weight and curing temperature of 25° C. for 48 hours.

Traditionally silicon wafers are used as the substrate for spin-coating of many liquid phase materials. PDMS shows significant adhesion to the silicon wafer after curing and hence peeling off the PDMS sheets from the wafers becomes difficult. Often this results in rupturing of sheets during peel off unless a sacrificial layer is applied on the silicon wafer prior to PDMS spin-coating. In this Example, ethanol-cleaned and air-dried, acrylic sheets (Optix, 2 mm thick, Plaskolite Inc.) were used as the substrate for spin-coating PDMS.

Figure 20A:
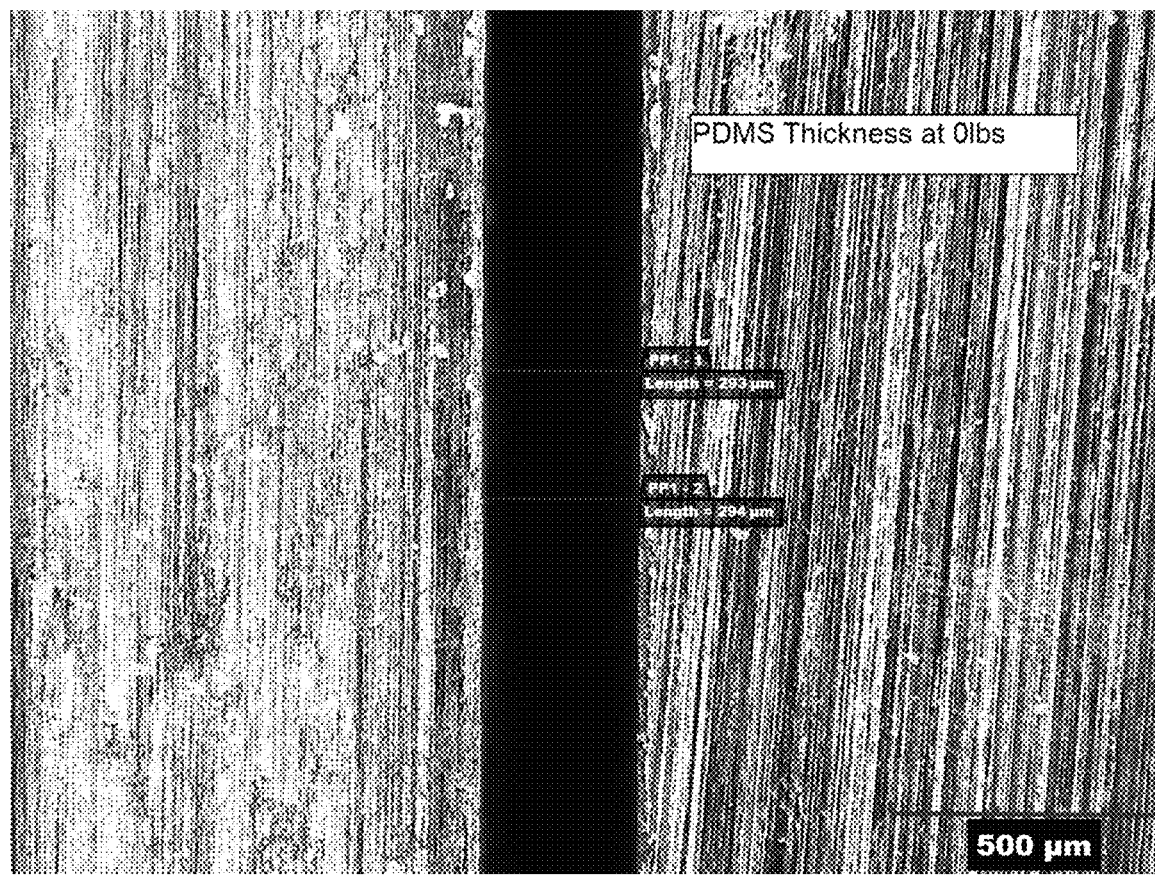
FIGS. 20A-20C are optical microscope images of PDMS elastomer (FIG. 20A) taken during compression at 0 lb, (FIG. 20B) taken during compression at 40 lbs, (FIG. 20C) taken during release of 40 lb.
Figure 20B:
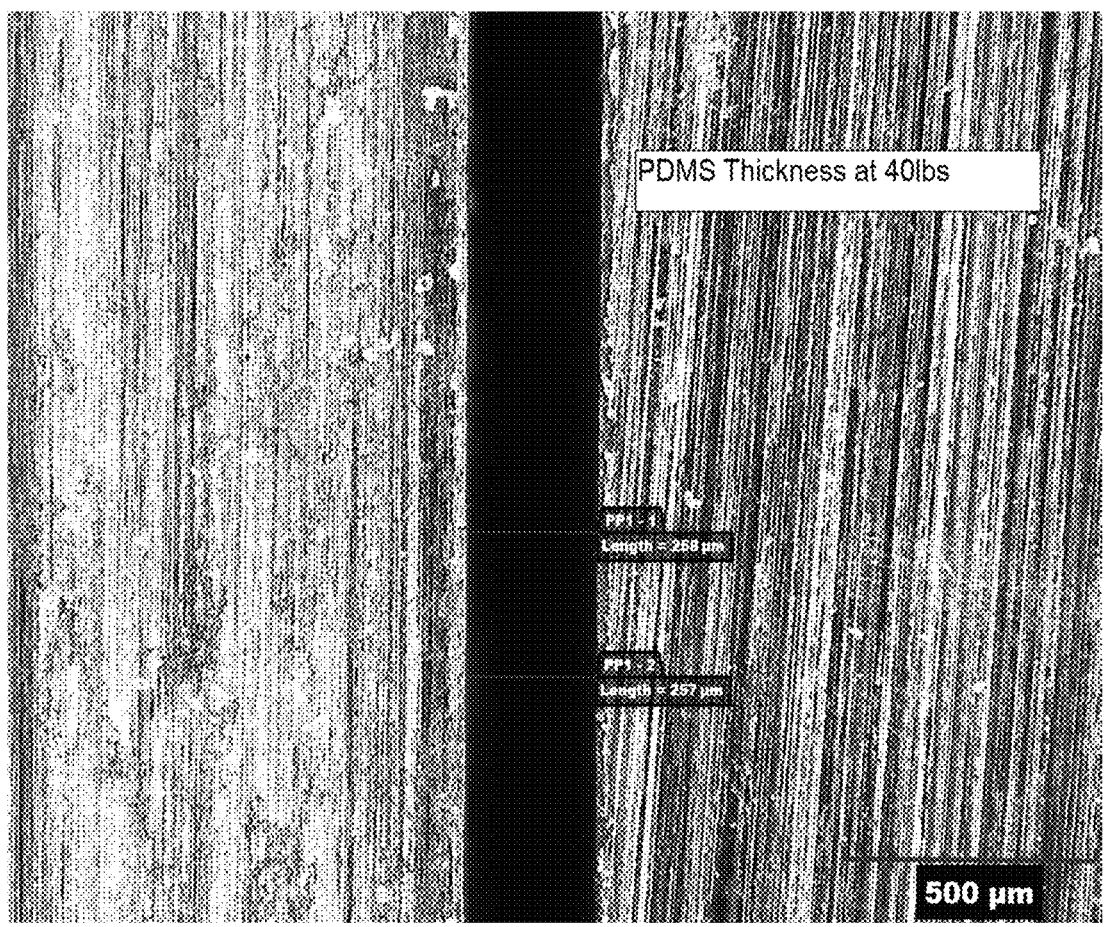
Figure 20C:
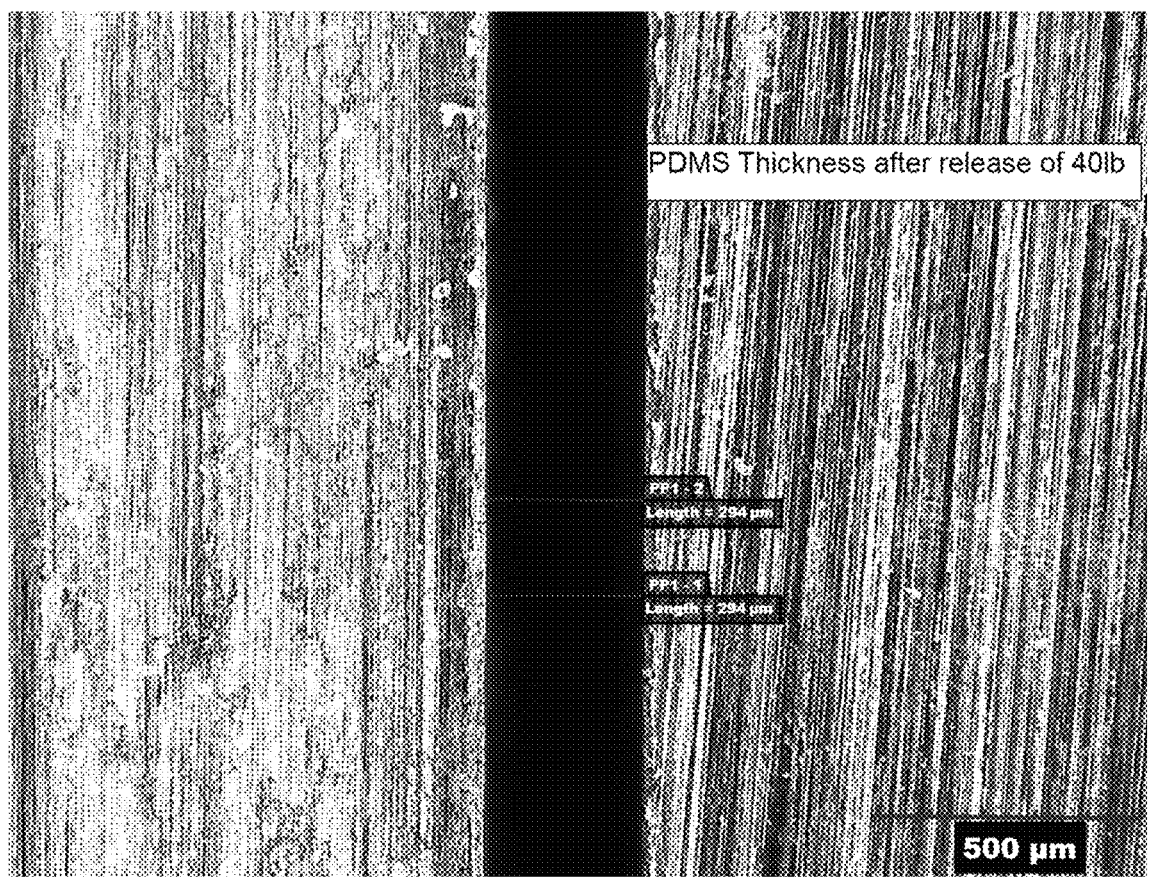
Figure 21:
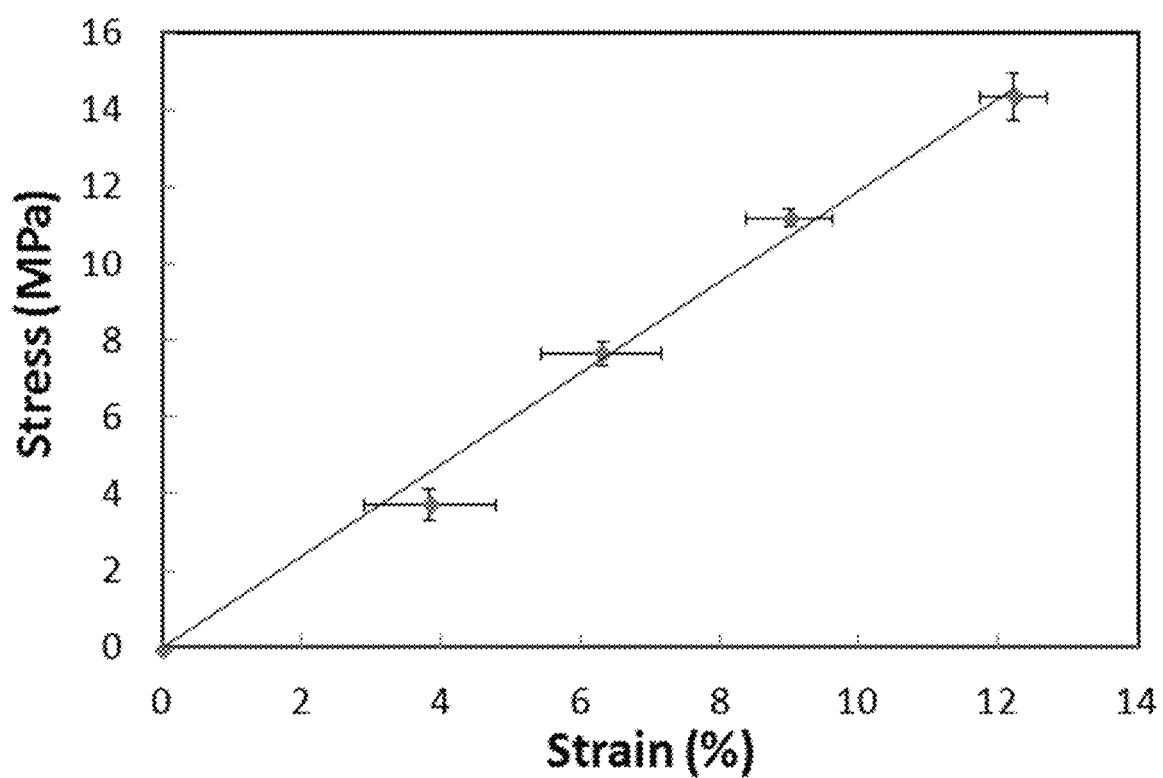
FIG. 21 depicts the compressive modulus of PDMS elastomer (thickness approximately 250 μm) used as pressure-sensitive element.

The CM plot of the elastomer was obtained by applying known compressive force to the elastomer sample manually using the precision vise and load cell to measure the corresponding deformation. FIGS. 20A-20C show photographic images of PDMS thickness taken by Hirox microscope at: no load applied (0 MPa) and then upon compression by with increasing load up to 14.35 MPa and finally after removal of the load. The strain developed at each stress value was graphically measured to generate the CM plot shown in FIG. 21. The CM was approximately 119 MPa which is in the same order obtained for PDMS samples prepared in accordance with American Society of International Association for Testing of Materials (ASTM) D575-91 standards. For this case, test specimens were approximately 28 mm in diameter and 12.5 mm thick and tested using ASTM D1229-03 (2008) methods to obtain a CM of approximately 187 MPa.

Figure 22:
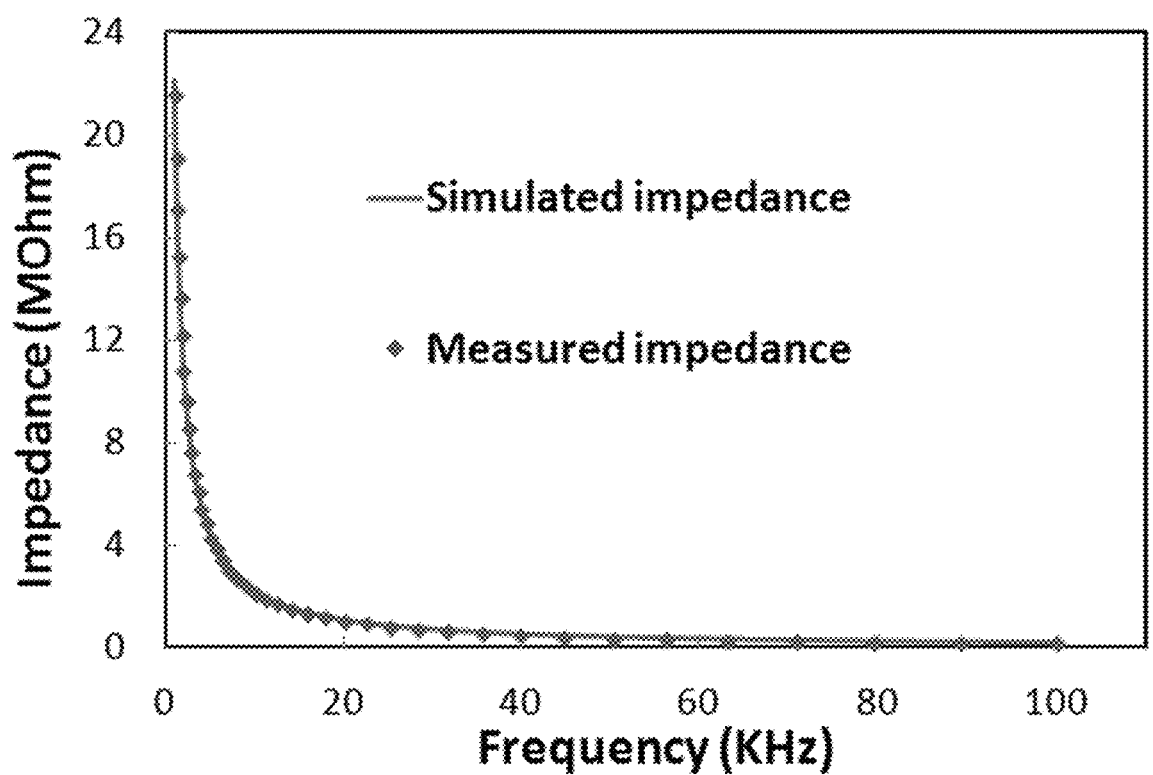
FIG. 22 depicts frequency vs. normalized impedance (at 500 mV rms).

FIG. 22 shows the typical frequency responses of three capacitive devices. A frequency sweep from 1 KHz to 100 KHz at 500 mV rms was given and the corresponding impedance values were measured and plotted by the impedance meter. These plots were in agreement with the mathematical equations to allow for the selection of a particular frequency to operate the device. Based on the geometry of capacitive device (thickness 250 μm, area 50.26 μm$^2$, ε 2.7), the calculated value of 7.5 pF was in similar range of 7.14 pF when measured.

All sensor data obtained in this Example was conducted at an operating frequency of 1 KHz although higher frequencies to 100 KHz were expected to work. Operating sinusoidal voltage around 100 mV rms generated approximately 3.48% output signal fluctuation due to system noise compared to 500 mV which generated fluctuation approximately 0.3%. Hence 500 mV was chosen as the operating voltage. Although in latter application higher rms voltages can be used as it will be beneficial in increasing signal-to-noise ratio.

Figure 23A:
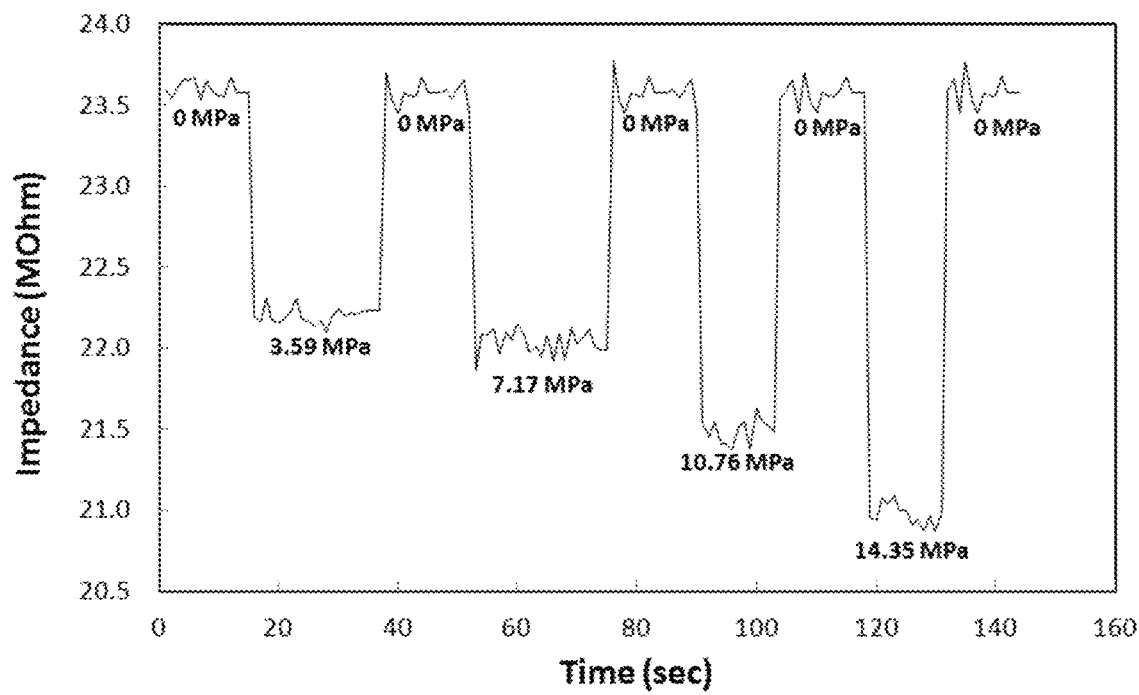
FIGS. 23A-23C depict time response plots of three devices carried out with operating sinusoidal voltage (500 mV rms, 1 KHz)).
Figure 23B:
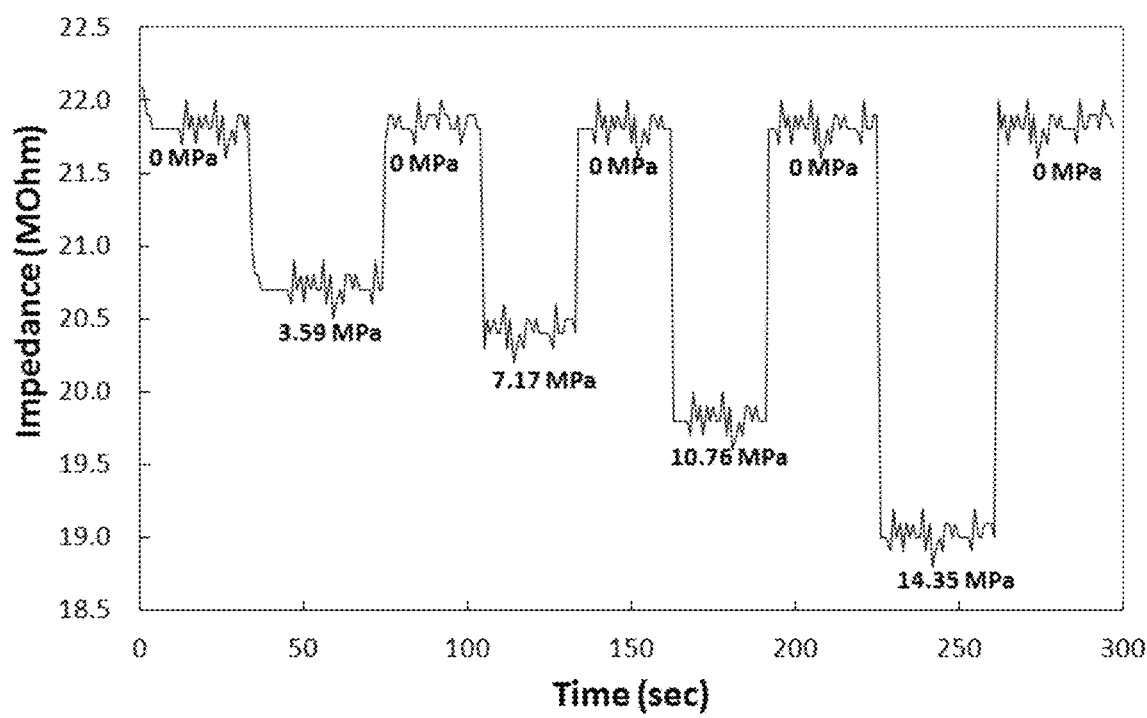
Figure 23C:
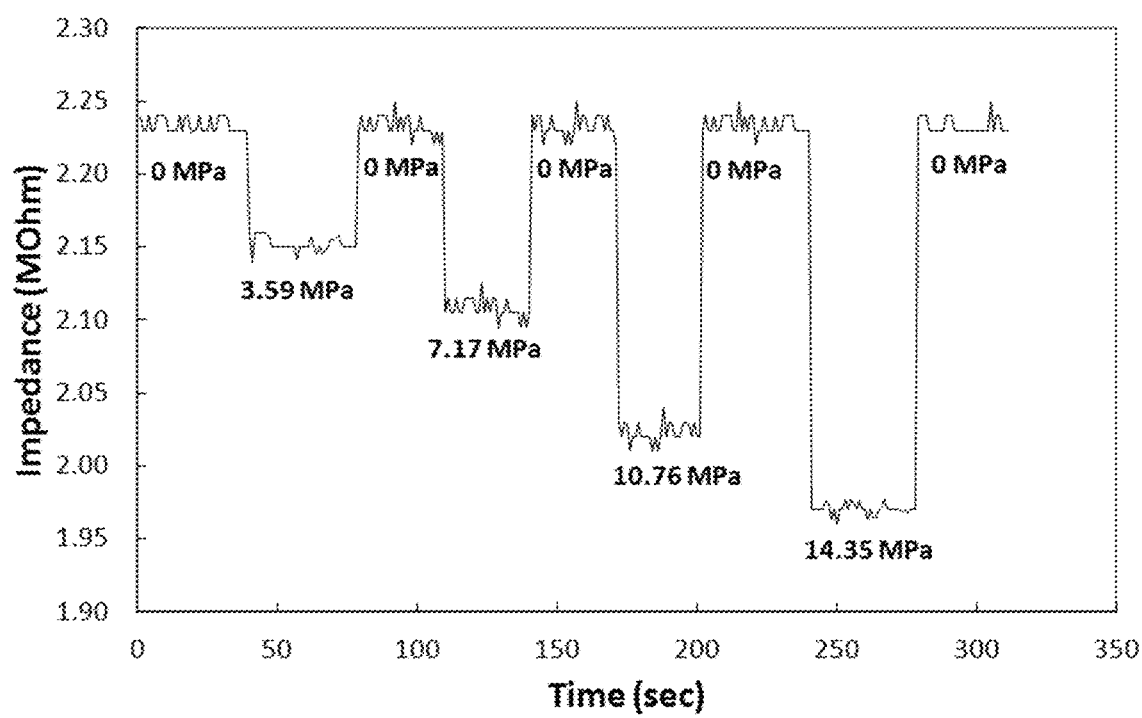

Time response plots are indicative of device's ability to respond to pressure application with respect to time. Time responses were obtained by repeated application of various known pressures between 3.59 MPa to 14.35 MPa (equivalent to 10 lb to 40 lb) manually applied with the precision vise. The measurements were carried out at 500 mV rms voltage and 1 KHz operating frequency. FIGS. 23A-23C show the time response of three devices. The lower impedance value regions indicate pressure was applied during that time interval leading to proportional decrease in impedance. The consequent recovery of impedance upon removal of pressure the original baseline reversibly indicated excellent shape memory retention of the elastomeric PDMS insulator serving as the pressure-sensitive element. The values of impedance for specific pressures were well in agreement to the CM plot of PDMS.

Figure 24:
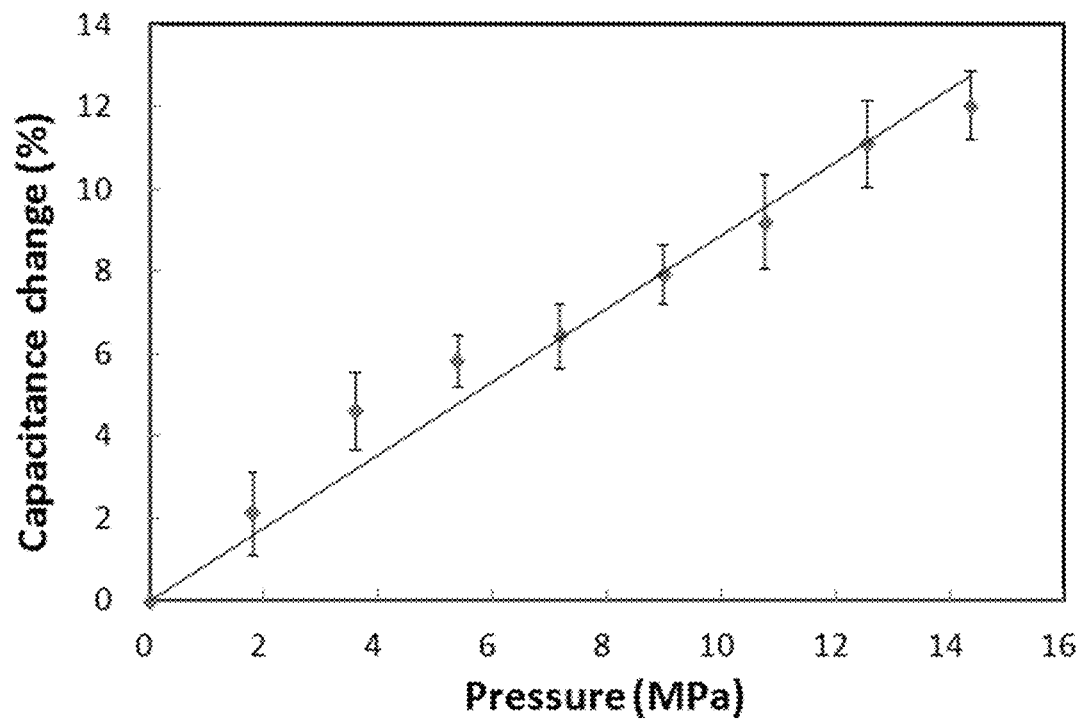
FIG. 24 depicts pressure sensitivity of five devices taken at 500 mV and 1 KHz operating frequency (n=5).

FIG. 24 shows the pressure sensitivity curve of devices where the percentage increase in capacitance was plotted for an increment of approximately 1.8 MPa (corresponds to 5 lbs) over a range of 0 MPa to 14.35 MPa (corresponds to 40 lbs). The percentage increase in capacitance for its corresponding pressure is well in accordance to the CM plot obtained for PDMS, thereby re-validating the device successful operation.

Figure 25A:
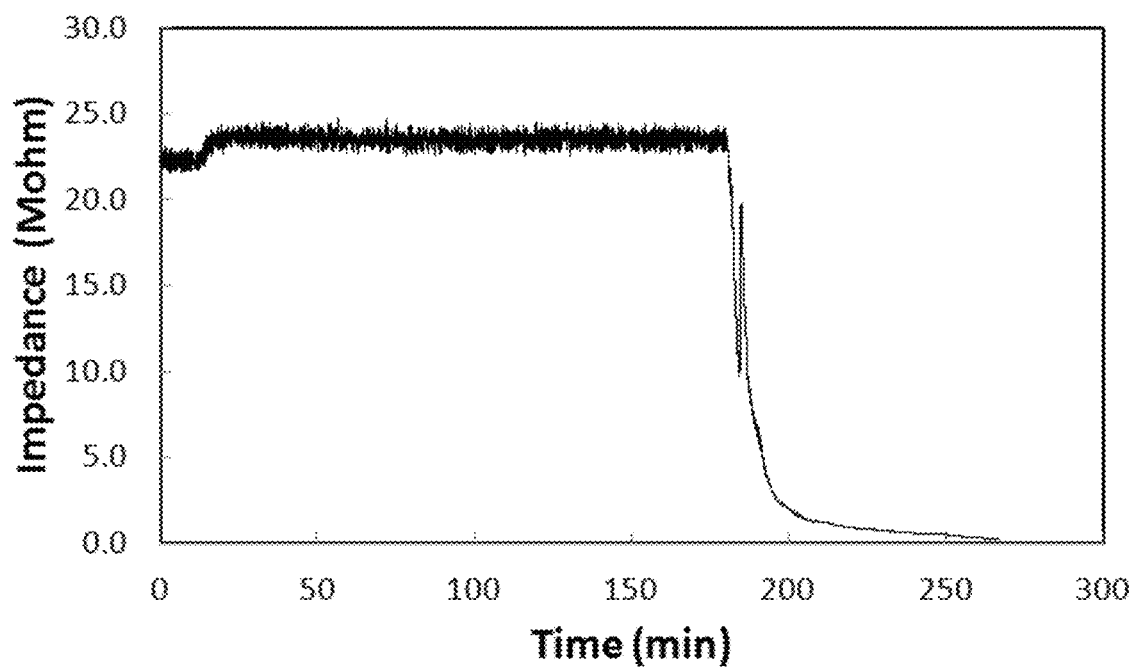
FIG. 25A depicts dissolution behavior of device in phosphate buffer solution (pH 7.4, 37° C.) to demonstrate the sudden failure (stage B to C in FIG. 1) with no applied pressure.

The time response was monitored during device dissolution. FIG. 25A shows that the device impedance maintained a constant level followed by steep decrease after approximately three hours. This demonstrates stages B-D of FIG. 1. The change demonstrated the expected behavior of rapid failure. During dissolution, the solution consumed the outer portion of the device thereby dismantling the structure. As a result, the two electrodes became short-circuited through the conductive solution and the impedance of the device was drastically reduced.

Figure 25B:
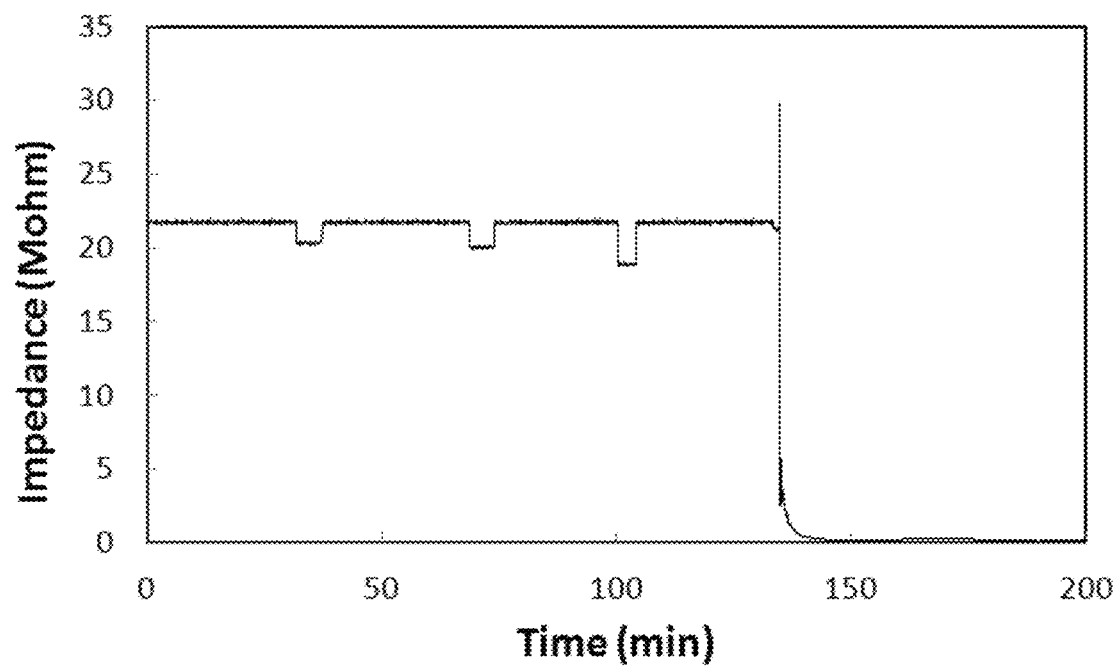
FIGS. 25B and 25C shows the device performance inside phosphate buffer solution when pressures were repeatedly applied at some regular time intervals in solution (pH 7.4, 37° C.).
Figure 25C:
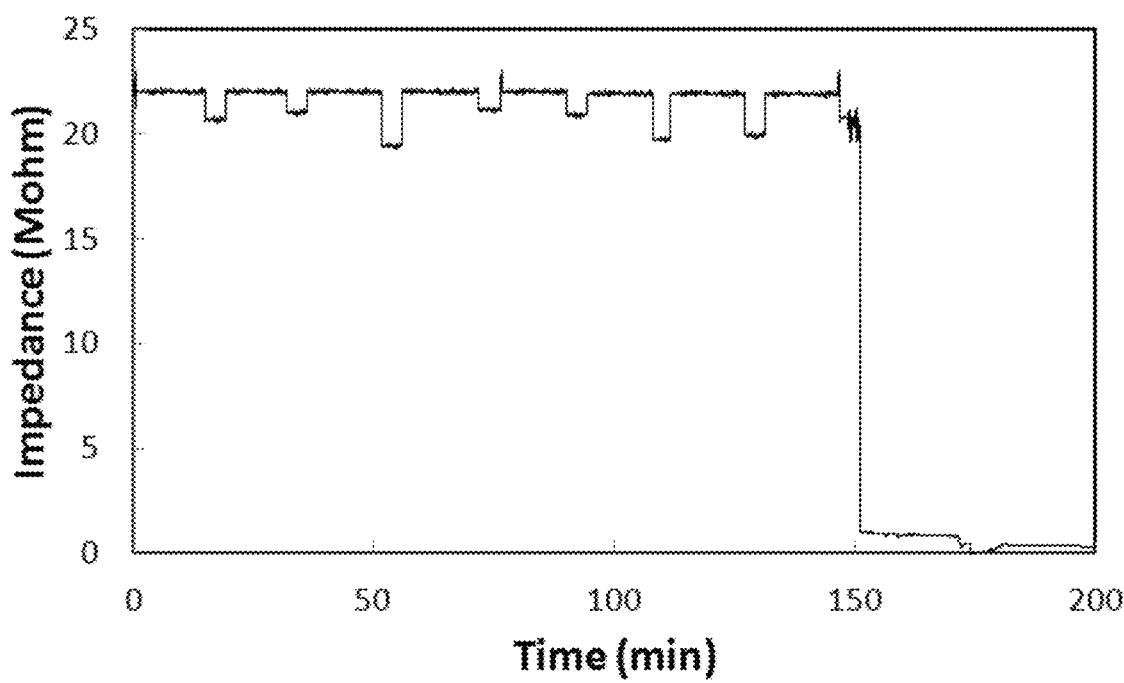

FIGS. 25B and 25C show the device performance inside solution when pressures were repeatedly applied at some regular time intervals. The low impedance region shows that pressure was applied for some time duration. The higher impedance region indicates that pressure was removed resulting in shape memory retention of the elastomeric PDMS in the capacitive device and hence resetting the device. After a few hours of periodic pressure application, the device impedance steeply decreased indicating the collapse of entire structure. This demonstrates that the device worked successfully under pressure application during the stage B to D followed by structural disintegration and consequent sudden failure.

The borate-based biodegradable glass material was successfully used as a novel functional platform to fabricate solid state sensors towards temporary implantation. The capacitive sensor responded to compressive pressure within range of approximately 14 MPa with good repeatability. The device remained operational for a short intended lifetime before it was disintegrated and finally dissolved, thereby validating the biodegradable sensors. Hence by optimizing design and fabrication parameters, it is expected to realize fully functional biodegradable devices during operational lifetime followed by rapid disintegration.

Example 4

Figure 26:
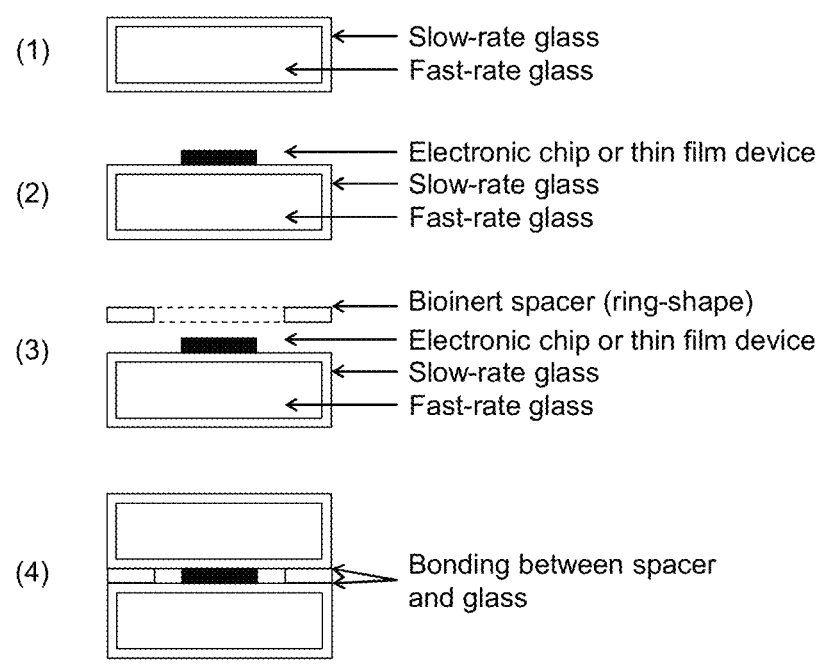
FIG. 26 depicts cross-sectional views of steps in the assembly of a degradable packaging assembly.

In this Example, a biodegradable packaging assembly for implanted electronic devices was prepared. The biodegradable packaging assembly was prepared using two glass substrates as illustrated in FIG. 26. One glass substrate served as mechanical carrier element of an implanted device, while a second glass substrate served as capping element. A ring-shaped spacer element was used to form a cavity to locate the electronic device. The spacer material can be the bioinert polymers, such as polydimethyl siloxane (PDMS). This spacer with a small volume, typically has a thickness about one millimeter and a diameter less than one centimeter, remains after all other elements are biodegraded. It does not cause any biohazard issue due to its bioinertness. The biodegradable packaging assembly can intentionally be degraded after a designed operational lifetime.

Although various biodegradable polymers are available, these organic materials are less ideal than their inorganic biodegradable glass counterparts in applications to device platforms described in the present disclosure. First, most biodegradable polymers exhibit a short degradation time upon implantation. Chemical compositions of the biodegradable glass materials of the present disclosure can be varied in an extremely wide range to tune the dissolution rate in biological environments (subnanometer to millimeter per day). Secondly, the hydrolysis (i.e. dissolution) of glass starts at the surface to be able to retain the original bulk properties until it is consumed and exhibits an intentional sudden failure, while that of polymers usually involves bulk hydration resulting in a gradual change of bulk properties over time. Third, mechanical properties of organic materials, in general, are not as viable as those of inorganic materials for many mechanical applications where stiffness is required. Most polymers exhibit Young's modulus values below several GPa, while those of glasses are in the order of several-ten to several-hundred GPa. Finally, polymers have a limited surface modification strategy, while the functionalization of inorganic surfaces (e.g. grafting self-assembled monolayer on glass) has been extensively studied and commonly practiced. The inorganic biodegradable glass materials of the present disclosure are superior in this respect.

What is claimed is:

1. A biodegradable electronic packaging assembly comprising:
    a first inorganic biodegradable substrate, wherein the first inorganic biodegradable substrate comprises a degradable glass selected from the group consisting of a borate-based glass, a phosphate-based glass, and combinations thereof and an electrode deposited on a surface of the first inorganic biodegradable substrate;
    a second inorganic biodegradable substrate comprises a degradable glass selected from the group consisting of a borate-based glass, a phosphate-based glass, and combinations thereof and an electrode deposited on a surface of the second inorganic biodegradable substrate; and
    an elastomeric insulator positioned between the first inorganic biodegradable substrate and the second inorganic biodegradable substrate;
    wherein at least one surface of at least one of the first inorganic biodegradable substrate and the second inorganic biodegradable substrate comprises a biodegradable silicate-based glass.

2. The biodegradable packaging assembly of claim 1, wherein a surface of the at least one of the first inorganic biodegradable substrate, the second inorganic biodegradable substrate, and the degradable silicate-based glass is silanized.

3. The biodegradable packaging assembly of claim 1, wherein the second inorganic biodegradable substrate substantially surrounds the first inorganic biodegradable substrate.

4. The biodegradable packaging assembly of claim 1, further comprising a bioinert spacer.

5. The biodegradable packaging assembly of claim 1, wherein at least one of the first inorganic biodegradable substrate is bonded with at least one of a spacer and the second inorganic biodegradable substrate.

* * * * *